US007067313B1

(12) United States Patent
Jacquemin et al.

(10) Patent No.: US 7,067,313 B1
(45) Date of Patent: Jun. 27, 2006

(54) LIGANDS FOR USE IN THERAPEUTIC COMPOSITIONS FOR THE TREATMENT OF HEMOSTASIS DISORDERS

(75) Inventors: Marc G. Jacquemin, Sart-Bernard (BE); Jean-Marie R. Saint-Remy, Grez-Doiceau (BE)

(73) Assignee: D. Collen Research Foundation, Leuven (BE)

( * ) Notice: Subject to any disclaimer, the term of this patent is extended or adjusted under 35 U.S.C. 154(b) by 291 days.

(21) Appl. No.: 10/030,522

(22) PCT Filed: Jul. 13, 2000

(86) PCT No.: PCT/EP00/06677

§ 371 (c)(1),
(2), (4) Date: May 2, 2002

(87) PCT Pub. No.: WO01/04269

PCT Pub. Date: Jan. 18, 2001

Related U.S. Application Data

(60) Provisional application No. 60/143,891, filed on Jul. 14, 1999.

(30) Foreign Application Priority Data

Jul. 14, 1999 (GB) .................... 9916450.1

(51) Int. Cl.
*C12N 5/20* (2006.01)
*C07K 16/00* (2006.01)
*C07K 16/36* (2006.01)

(52) U.S. Cl. ............... 435/326; 530/387.1; 530/388.25

(58) Field of Classification Search ........... 530/388.25, 530/387.3, 387.1; 424/13.1, 145.1; 435/326
See application file for complete search history.

(56) References Cited

U.S. PATENT DOCUMENTS 5,602,015 A * 2/1997 Sudhir
5,744,446 A * 4/1998 Lollar et al.
6,210,675 B1 * 4/2001 Highfield et al.

FOREIGN PATENT DOCUMENTS

WO  WO 97 26010  7/1997

OTHER PUBLICATIONS

Lenting et al. Identification of a binding site for blood coagulation factor IXa on the light chain of human factor VIII. J. Biol Chem 269(10):7150-7155, 1994.*
Peerlinck et al. Antifactor VIII antibody inhibiting allogeneic but not autologous factor VIII in patients with mild hemophilia A. Blood. 93(7):2267-2273, Apr. 1999.*
Gilles et al. Mutation Arg2150-His in the factor VIII C1 domain alters the binding of factor VIII to von Willebrand factor and is responsible for a mild hemophilia A phenotype. Blood vol. 92, 10Suppl. 1 Part 1-2, pp. 710., Nov. 15, 1998.*
J. Batlle et al. : "Alloantibody from a patient with severe von Willebrand disease inhibits von Willebrand factor-FVIII interaction." Annals of Hematology, vol. 75, No. 3, Sep. 1997, pp. 111-115, XP 000906715.
J. Ingerslev et al.: "Applications of immunoperoxidase techniques in specificity testing of monoclonal antibodies (Mabs) against von Willebrand factor (vWF)." Clinica Chemica Acta, vol. 174, No. 1, 1988, pp. 65-82, XP000906709.
M. Gawryl et al.: "Inactiviation of factor VIII coagulant activity by two different types of human antibodies." BLOOD, vol. 60, No. 5, Nov. 1982, pp. 1103-1109, XP000892192.
B. Ly et. al.: "Characterization of an antibody to factor VIII in a patient with acquired hemophilia with circulating immune complexes." Scandinavian Journal of Haematology, vol. 28, No. 2, Feb. 1982, pp. 132-140, XP000892196.
M. Jacquemin et al.: "Mechanism and kinetics of factor VIII inactivation: Study with an IgG4 monoclonal antibody derived from a hemophilia A patient with inhibitor." BLOOD, vol. 92, No. 2, Jul. 15, 1998, pp. 496-506, XP000906844.
M Jacquemin et al.: "A human antibody directed to the factor VIII C1 domain inhibits factor VIII cofactor activity and binding to von Willebrand factor." BLOOD, vol. 95, No. 1, Jan. 1, 2000, pp. 156-163, XP002150704.

* cited by examiner

Primary Examiner—Christina Chan
Assistant Examiner—Maher Haddad
(74) Attorney, Agent, or Firm—Clark & Elbing LLP

(57) ABSTRACT

The present invention comprises ligands and methods of manufacture thereof as well as pharmaceutical preparations including the ligands. The ligands may be human or humanized monoclonal antibodies and fragments, derivatives and homologs thereof. These may exhibit an unforeseen "plateau effect", i.e. the achievement of only a partial inactivation of a factor involved in hemostasis, in particular in the coagulation cascade, either individually or in combination even in molar excess. The ligands may bind to a factor or a complex of factors resulting in only partially impairing the function of a physiologically functional site of the said factor or factor complex even in molar excess. This makes the ligands particularly suitable for treating coagulation disorders and resulting thrombotic pathologic conditions while minimizing the risk of bleeding. Particularly useful is a property of ligands in accordance with the present invention to allow some physiological function of the affected site even when the ligand is in molar excess. The ligands may be anti-factor VIII antibodies or antibodies against a factor VIII complex, in particular human or human hybrid monoclonal antibodies which bind to factor VIII or a factor VIII complex and at least partially inhibit the activity of factor VIII.

3 Claims, 11 Drawing Sheets

```
1/1                                                        31/11
atg gac tgg acc tgg agg atc ctc ttg gtg gca gca gct aca ggc acc cac gcc cag
Met asp trp thr trp arg ile leu phe leu val ala ala thr gly thr his ala gln 61/21                                                      91/31
gtc caa ctg gta cag tct ggg gct gag gtg aag aag cct ggg gcc tca gtg aag gtc tcc
val gln leu val gln ser gly ala glu val lys lys pro gly ala ser val lys val ser 121/41                                                     151/51
tgc aag gtt tcc gga tac acc ctc act gaa tta ccc gtg cac tgg gta cag cag gct cct
cys lys val ser gly tyr thr leu thr glu leu pro val his trp val gln gln ala pro
             <----------------CDR 1---------------->

181/61                                                     211/71
gga aaa ggg ctt gag tgg gtg gga agt ttt gat cct gaa agt gga gaa tca atc tac gca
gly lys gly leu glu trp val gly ser phe asp pro glu ser gly glu ser ile tyr ala
                                    <--------------------CDR 2-----

241/81                                                     271/91
cgg gag ttc cag ggc agc gtc acc atg acc aca tct aca gac ata gcc tac atg
arg glu phe gln gly ser val thr met thr ser thr asp ile ala tyr met
------------------------------>

301/101                                                    331/111
gag ctg agc agc ctg aga tct gac gac acg gcc gtg tat tac tgt gca gtc cct gac cct
glu leu ser ser leu arg ser asp asp thr ala val tyr tyr cys ala val pro asp pro 361/121                                                    391/131
gat gct ttt gat ata tgg ggc caa ggg aca atg gtc acc gtc tct tca gcc tcc acc aag
asp ala phe asp ile trp gly gln gly thr met val thr val ser ser ala ser thr lys
---CDR 3------------>

421/141
ggc cca tcg gtc ttc ccc ctg gga tcc agt    (SEQ ID NO:5)
gly pro ser val phe pro leu gly ser arg    (SEQ ID NO:2)
```

1/1
atg gaa acc cca gct cag ctt ctc ttc ctc cta ctc tgg ctc tca gat acc acc gga
Met glu thr pro ala gln leu leu phe leu leu trp leu ser asp thr thr gly

31/11

61/21
gaa att gcg ttg acg cag tct cca ggc acc ctg tct ttg tct cca ggg gaa aga gcc acc
glu ile ala leu thr gln ser pro gly thr leu ser leu ser pro gly glu arg ala thr

91/31

121/41
ctc tcc tgc agg gcc agt cag agt ttt agc agc tac tta gcc tgg tat cag cag aaa
leu ser cys arg ala ser gln ser phe ser ser tyr leu ala trp tyr gln gln lys
<----------------CDR 1---------------->

151/51

181/61
cct ggc cag gct ccc agg ctc ctc atc tat ggt gca tcc acc agg gcc act ggc atc cca
pro gly gln ala pro arg leu leu ile tyr gly ala ser thr arg ala thr gly ile pro
                                    <---------CDR 2---------->

211/71

241/81
gac agg ttc agt ggc agt ggg tct ggg aca gac ttc act ctc acc atc agc aga ctg gag
asp arg phe ser gly ser gly ser gly thr asp phe thr leu thr ile ser arg leu glu

271/91

301/101
cct gaa gat ttt gca gtg tat tac tgt cag cag tat ggt acg tca gcg atc acc ttc ggg
pro glu asp phe ala val tyr tyr cys gln gln tyr gly thr ser ala ile thr phe gly
                                    <---------CDR 3---------->

331/111

361/121
caa ggg aca cga ctg gag att aaa gga act gtg gct gca cca tct gtc ttc atc ttc ccg
gln gly thr arg leu glu ile lys gly thr val ala ala pro ser val phe ile phe pro

391/131

421/141
cca tct   (SEQ ID NO:6)
pro ser   (SEQ ID NO:3)

FIG. 8

VH Krlr-1 (Figure 8)

1/1                                                                31/11
ATG GAC TGG ACC TGG AGG ATC CTC TTC TTG GTG GCA GCA ACA GGA GCC CAC TCC CAG
Met Asp Trp Thr Trp Arg Ile Leu Phe Leu Val Ala Ala Thr Gly Ala His Ser Gln

61/21                                                              91/31
GTG CAA CTG GTG CAA TCT GGG GCT GAG GTG AAG AAG CCT GGG GCC TCA GTG AAG GTC TCC
Val Gln Leu Val Gln Ser Gly Ala Glu Val Lys Lys Pro Gly Ala Ser Val Lys Val Ser

121/41                                                             151/51
TGC AAG ACC TCT GGA TAC AAC TTC ACC GGC TAC TCT GCT TCT GGA CAT ATC TTC ACC GCC
Cys Lys Thr Ser Gly Tyr Asn Phe Thr Gly Tyr Ser Ala Ser Gly His Ile Phe Thr Ala
                                                          <------CDR1------

181/61                                                             211/71
TAC TCT GTG CAC TGG GTG CGA CAG GCC CCT GGA CAA GGG CTT GAG TGG ATG GGA AGG ATC
Tyr Ser Val His Trp Val Arg Gln Ala Pro Gly Gln Gly Leu Glu Trp Met Gly Arg Ile
------>

41/81                                                              271/91
AAC CCT AAC AGT GGT GCC ACA GAC TAT GCA CAT AAA TTT CAG GGC AGG GTC ACC ATG TCC
Asn Pro Asn Ser Gly Ala Thr Asp Tyr Ala His Lys Phe Gln Gly Arg Val Thr Met Ser
------CDR2------------------------>

```
AGG GAC ACG TCC ATC AGC ACA GCC TAC ATG GAA CTG AGC AGG CTG ACA TCT GAC GAC ACG
Arg Asp Thr Ser Ile Ser Thr Ala Tyr Met Glu Leu Ser Arg Leu Thr Ser Asp Asp Thr

361/121                                         391/131
GCC ATG TAT TAC TGT GCG AGA GCC GAC AAC TAT TTC GAT ATT GTG ACT GGT TAT ACT TCT
Ala Met Tyr Tyr Cys Ala Arg Ala Asp Asn Tyr Phe Asp Ile Val Thr Gly Tyr Thr Ser
                                                        <-------CDR3

421/141                                         451/151
CAT TAC TTT GAC TAC TGG GGC CGG GGA ACC CTG GTC ACC GTC TCC TCA    (SEQ ID NO:7)
His Tyr Phe Asp Tyr Trp Gly Arg Gly Thr Leu Val Thr Val Ser Ser   (SEQ ID NO:8)
-------->
```

FIG. 9

VL KRIX 1

```
1/1
ATG GAA ACC CCA GCT CAG CTT CTC TTC CTC CTG CTA CTC TTC TGG CTC CCA GAT ACC ACC GGA
Met glu thr pro ala gln leu leu phe leu leu leu leu phe trp leu pro asp thr thr gly 61/21
GAA ATT GTG TTG ACG CAG TTC CCA GGC ACC CTG TCT TTG TCT CCA GGG GAA AGA GCC ACC
glu ile val leu thr gln phe pro gly thr leu ser leu ser pro gly glu arg ala thr 121/41
CTC TCC TGC AGG GCC AGT CAG AGT GTT GCC AGC TAC TTA GCC TAC CAG CAA AAA
leu ser cys arg ala ser gln ser val ala ser tyr leu ala trp tyr gln gln lys
                    <---------------CDR 1-------------->

181/61
CCT GGC CAG GCT CCC AGG CTC CTC ATC TAT GGT GCA TCC AGT AGG GCC ACC GAC ATC CCA
pro gly gln ala pro arg leu leu ile tyr gly ala ser ser arg ala thr asp ile pro
                                    <-----------CDR 2----------->

241/81
CAC AGG TTC AGT GGC AGT GGG TCT GGG ACA GAC TTC ACT CTC ACC ATC AGC AGA CTG GAG
his arg phe ser gly ser gly ser gly thr asp phe thr leu thr ile ser arg leu glu 301/101
CCT GAA GAT TTT GCA GTG TAC TAC TGT CAG CAA TAT GGT ACC TCA GCC TTA CTC ACT TTC
pro glu asp phe ala val tyr tyr cys gln gln tyr gly thr ser ala leu leu thr phe
                                                <---------------CDR 3-------

391/131
GGC GGA GGG ACC AAG GTG GAG ATC AAA CGA ACT GTG GCT GCA CCA TCT GTC TTC ATC TTC
gly gly gly thr lys val glu ile lys arg thr val ala ala pro ser val phe ile phe
    -------->

421/141
CCG CCA TCT    (SEQ ID NO:4)
pro pro ser    (SEQ ID NO:1)
```

LIGANDS FOR USE IN THERAPEUTIC COMPOSITIONS FOR THE TREATMENT OF HEMOSTASIS DISORDERS

CROSS REFERENCE TO RELATED APPLICATIONS

This application is the U.S. National Stage of International Application No. PCT/EP00/06677, filed Jul. 13, 2000, which, in turn, claims the benefit of U.S. provisional patent application Ser. No. 60/143,891, filed Jul. 14, 1999.

FIELD OF THE INVENTION

The present invention relates to novel cell lines and to ligands, namely human and/or humanized monoclonal antibodies, as well as fragments such as Fab, Fab', F(ab')$_2$, scFv, single variable domains, complementarity determining regions, derivatives, homologs and combinations thereof, obtainable from the said cell lines. It also relates to pharmaceutical compositions comprising said ligands and to methods of preventing and treating coagulation disorders and resulting thrombotic pathologic conditions in humans by administration of the said ligands to patients in need thereof. It also relates to methods of obtaining specific mammalian antibodies.

BACKGROUND OF THE INVENTION

The formation of blood clots does not only limit bleeding in case of an injury (hemostasis), but may lead to serious organ damage and death in the context of atherosclerotic diseases by occlusion of an important artery or vein. Thrombosis is thus blood clot formation at the wrong time and place. It involves a cascade of complicated and regulated biochemical reactions between circulating blood proteins (coagulation factors), blood cells (in particular platelets) and elements of an injured vessel wall. Anticoagulation and antithrombotic treatment aim at inhibiting the formation of blood clots in order to prevent these dangerous consequences, such as myocardial infarction, stroke, loss of a limb by peripheral artery disease or pulmonary embolism. Given the importance of these diseases, it is rather surprising that antithrombotic therapy has relied on a few drugs since many years, namely Aspirin to inhibit platelets, Heparin that indirectly inhibits the coagulation factors IX, X and II (thrombin), and oral Warfarin that inhibits Vit K-dependent factors (VI, IX, X, II and Prot C). More recently, low molecular weight Heparins (inhibiting factors X and II to various degrees) have become anticoagulants of choice, largely because of their ease of application (once a day subcutaneous injection with no monitoring need). With growing understanding of the processes involved in thrombosis a growing number of specific inhibitors of coagulation factors have been developed. However, a better efficacy/safety ratio could to date not be obtained with them. Direct thrombin inhibitors, in particular, were linked to increased bleeding complications in large clinical trials.

Aspirin also provides a protective effect against thrombosis. It induces a long-lasting functional defect in platelets, detectable clinically as a prolongation of the bleeding time, through inhibition of the cyclooxygenase activity of the human platelet enzyme prostaglandin H-synthase (PGHS-1) with doses as low as 30 to 75 mg. Since gastrointestinal side effects of aspirin appear to be dose-dependent, and for secondary prevention, treatment with aspirin is recommended for an indefinite period, there are practical reasons to choose the lowest effective dose. Further it has been speculated that a low dose (30 mg daily) might be more anti-thrombotic but attempts to identify the optimal dosage have yielded conflicting results. It has been claimed that the dose of aspirin needed to suppress fully platelet aggregation may be higher in patients with cerebrovascular disease than in healthy subjects and may vary from time to time in the same patient. However, aspirin in any daily dose of 30 mg or higher reduces the risk of major vascular events by 20% at most, which leaves much room for improvement.

Further, the inhibiting role of aspirin may lead to prevention of thrombosis as well as to excess bleeding. The balance between the two depends critically on the absolute thrombotic versus hemorrhage risk of the patient.

In patients with acute myocardial infarction, reduction of infarct size, preservation of ventricular function and reduction in mortality has been demonstrated with various thrombolytic agents. However these agents still have significant shortcomings, including the need for large therapeutic doses, limited fibrin specificity, and significant associated bleeding tendency. Recombinant tissue plasminogen activator (t-PA) restores complete patency in just over one half of patients, whereas streptokinase achieves this goal in less than one third. Further, reocclusion after thrombolytic therapy occurs in 5 to 10% of cases during the hospital stay and in up to 30% within the first year according to Verheugt et al., *J. Am. Coll. Cardiol.* (1996) 27:618–627. Thus numerous studies have examined the effects of adjunctive antithrombin therapy for patients with acute myocardial infarction. As an example, U.S. Pat. No. 5,589,173 discloses a method for dissolving and preventing reformation of an occluding thrombus comprising administering a tissue factor protein antagonist, which may be a monoclonal or polyclonal antibody, in adjunction to a thrombolytic agent.

Monoclonal antibodies have already been shown to be of therapeutic value as antithrombotic agents. The first approved drug in this field was Abciximab (ReoPro™), a humanized Fab fragment of a murine monoclonal antibody (7E3) against platelet GP IIbIIIa receptors. Murine antibodies have characteristics which may severely limit their use in human therapy. As foreign proteins, they may elicit an anti-immunoglobulin response termed human anti-mouse antibody (HAMA) that reduces or destroys their therapeutic efficacy and/or provokes allergic or hypersensitivity reactions in patients, as taught by Jaffers et al., *Transplantation* (1986) 41:572. The need for readministration in therapies of thromboembolic disorders increases the likelihood of such immune reactions. While the use of human monoclonal antibodies would address this limitation, it has proven difficult to generate large amounts of such antibodies by conventional hybridoma technology.

Recombinant technology has therefore been used to construct "humanized" antibodies that maintain the high binding affinity of murine monoclonal antibodies but exhibit reduced immunogenicity in humans. In particular, there have been suggested chimeric antibodies in which the variable region (V) of a non-human antibody is combined with the constant (C) region of a human antibody. As an example, the murine Fc fragment was removed from 7 E3 and replaced by the human constant immunoglobulin G Fab region to form a chimera known as c7 E3 Fab or abciximab. Methods of obtaining such chimerical immunoglobulins is described in detail in U.S. Pat. No. 5,770,198.

The potential for synergism between GPIIb/IIIa inhibition by monoclonal antibody 7 E3 Fab and thrombolytic therapy was evaluated by Kleiman et al., *J. Am. Coll. Cardiol* (1993) 22:381–389. Major bleeding was frequent in this study.

Hence, the potential for life-threatening bleeding is clearly a major concern with this combination of powerful anti-thrombotic compounds.

In a recent attempt to reduce the immunogenicity of murine antibodies, only the complementarity determining region (CDR), i.e. regions of hypervariability in the V regions, rather than the entire V domain, are transplanted to a human antibody. Such humanized antibodies are known as CDR-grafted antibodies. Such one CDR-grafted antibody was successfully constructed against the relatively simple nitrophenacetyl antigen, however the construction of CDR-grafted antibodies recognizing more complex antigens has resulted in antibodies having binding activity significantly lower than the native non-human antibodies. In numerous cases it was demonstrated that the mere introduction of non-human CDRs into a human antibody is insufficient to maintain full binding activity. While a refined computer model of the murine antibody of interest is required in order to identify critical amino-acids to be considered in the design of a humanized antibody, and general theoretical guidelines were proposed for such design, in all cases the procedure must be tailored and optimized for the particular non-human antibody of interest.

Tissue factor (TF), being a membrane glycoprotein functioning as a receptor for factor VII and VIIa and thereby initiating the said extrinsic pathway, has been investigated as a target for anticoagulant therapy. In addition to this role, TF has been implicated in pathogenic conditions such as vascular disease and gram-negative septic shock. A study attempting to characterize the anticoagulant potential of murine monoclonal antibodies showed that the inhibition of TF function by most of the monoclonal antibodies assessed was dependent upon the dissociation of the TF/VIIa complex that is rapidly formed when TF contacts plasma One monoclonal antibody, TF8-5G9, was capable of inhibiting the TF/VIIa complex without dissociation of the complex, thus providing an immediate anticoagulant effect in plasma, as disclosed in WO 96/40,921.

Targeted clotting factors exhibit both a medium molecular weight range (about 45,000 to 160,000) and a relatively high normal plasma concentration (at least 0.01 micromol/L).

One persistent concern with all available anti-thrombotic agents is the risk of overdose and therefore of excessive and life-threatening bleeding. Most current antithrombotic agents therefore warrant close monitoring of the patient.

Thus, there is a need for efficient compounds for the treatment of coagulation disorders, which cannot be overdosed, require no monitoring and are free from bleeding problems. For a therapeutic agent based on antibodies, the ideal compound would be a human antibody with full anticoagulant efficacy that does not induce immunogenicity.

Factor VIII is a protein providing important coagulant cofactor activity and is one of human clotting factors with a rather high molecular weight (265,000) and a very low normal plasma concentration (0.0007 micromol./liter). With its 2,332 amino-acid residues, factor VIII is one of the longest known polypeptide chains and is synthesized in the liver, the spleen and the placenta. Its gene has been shown to include 186,000 nucleotides.

Factor VIII circulates as inactive plasma protein. Factors V and VIII are homologous proteins sharing a common structural configuration of triplicated A domains and duplicated C domains with structurally divergent B domains connecting the A2 and A3 domains. Factor VIII circulates in a multiplicity of fragmented species in a tightly associated complex with von Willebrand factor at a concentration of 1 mmol/L. Factor VIII activation occurs by a cleavage between the A1 and A2 domains, resulting in the unstable heterotrimeric factor VIIIa molecule. Factor VIIIa binds tightly to membranes that contain acidic phospholipids. Factor VIII contains a phospholipid binding site in the C2 domain, between amino-acids 2302 and 2332, according to Arai et al. in *J. Clin. Invest.* (1989) 83:1978. Within the same factor VIII region, there is also a von Willebrand factor binding site acting in conjunction with amino-acid residues 1645–1689 in the A3 domain according to Shima et al. in *Throm. Haemost.* (1993) 69:240 and *J. Biol. Chem.* (1994) 269:11601.

Polyclonal antibodies inhibiting the co-factor activity of factor VIII have been classified as type I or type II inhibitors according to their capacity to inhibit factor VIII either completely (type I) or only partially (type II). According to Gawryl et al., *Blood* (1982) 60:1103–9, the reduced inactivation of factor VIII by human type II autoantibodies is believed to be due to a steric effect of von Willebrand factor. Monoclonal antibodies are not mentioned and, to date, no therapeutic use was made of such type II inhibitors. Biggs et al., *Br. J. Haematol.* (1972) 23:137 previously provided an interpretation derived from data obtained by using human polyclonal antibodies, that a type II inhibitory pattern could be related to low affinity. B. Ly et al., *Scandinavian Journal of Haematology* (1982), 28:132–140 discloses polyclonal antibodies to factor VIII which most often belong to the IgG class both in hemophiliacs developing alloantibodies and in the more rare patients having autoantibodies against their own factor VIII. These polyclonal antibodies partially inactivate Factor VIII activity like the antibodies described in Biggs et al. (1972) and Hoyer et al. (1982), This document again fails to mention whether monoclonal antibodies can reproduce the pattern of Factor VIII inactivation shown by patient's polyclonal antibodies. Again, no monoclonal antibodies are mentioned.

European patent applications EP-A-123,945, EP-A-152, 746 and EP-A432,134 all disclose monoclonal antibodies produced by hybridoma cell lines and having a specific reactivity pattern with factor VIIIc polypeptide fragments. These monoclonal antibodies are said to be useful for detecting the presence of factor VIIIc and related polypeptides in plasma by immunoassay techniques, but a-therapeutic potential use is not suggested in these documents.

J. Battle et al., *Annals of Hematology* (1997) 75:111–115, discloses a polyclonal alloantibody from a patient with severe von Willebrand disease showing, alike a rabbit polyclonal antibody against von Willebrand factor, a partial inhibitory activity to plasma Factor VIII. These polyclonal anti-factor VIII antibodies therefore inactivate factor VIII following a pattern similar to anti-factor VIII type II antibodies found in patients with hemophilia A (Gawryl et al., *Blood* (1982) 60:1103–9). However, factor VIII antibodies were not detected in the said human alloantibody, thus suggesting that it was a non specific inhibition.

J. Ingerslev et al., *Clinica Chimica Acta* (1988) 174:65–82 discloses a series of murine monoclonal antibodies against human von Willebrand factor: two of them, belonging to the immunoglobulin isotype IgG1, exhibit an extremely low (1.3 BU/mg immunoglobulin) inhibition of factor VIII as shown in table I of said document. By comparison, human monoclonal antibody BO2C11, derived from a hemophilia A patient with inhibitor, has a specific activity of 7,000 BUI mg protein (Jacquemin et al. *Blood*, (1998) 92:496–506). This indicates that administration of antibodies as described by Ingerslev to an animal or a human being would not affect factor VIII activity, unless an extremely high amount of antibody (hundreds of mg/ml) was present in plasma. The authors do not disclose whether when used in large excess these antibodies exhibit inhibitory activity like type I or type II (i.e. partial inactivation) polyclonal human factor VIII inhibitor, such as described in Gawryl et al., *Blood* (1982) 60:1103–9.

Maraganore et al., *Circulation* (1992) 86:413, showed that a synthetic 12-aminoacid peptide corresponding to residues 1675–1686 of factor VIII inhibits cleavage by thrombin of the heavy chain required for the activation of the procoagulant activity of factor VIII and also of the light chain required to dissociate factor VIII from von Willebrand factor and that tyrosine sulfation of said peptide potentiates its recognition by factor VIII.

*J. Clin. Invest.* (1988) 82:206–211 describes obtaining an animal model for hemophilia A by infusion of human anti-factor VIII antibody in rabbits. According to WO 95/01570, antibodies against the light chain of human or porcine factor VIIIc were produced in a first animal and subsequently a temporary hemophilia was induced in a second animal by means of the purified monospecific antibody obtained. U.S. Pat. No. 5,804,159 also discloses inducing a temporary clotting disorder in a mammal by means of an anti-plasma antibody preparation acting on several blood coagulation factors, e.g. a preparation comprising antibodies against human von Willebrand factor and factor VIII, or against factor VIII/von Willebrand factor-complex, or against procoagulants, anticoagulants, clot structure factors, fibrinolysis factors and phospholipids.

However, none of the above-mentioned antibodies compounds involving factor VIII have been described for therapeutic purposes. In fact there is a prejudice among those skilled in the art against investigating anti-factor VIII antibodies for anti-thrombotic therapy because it is assumed that, a deficiency in factor VIII being the cause of hemophilia A, such antibodies would induce a bleeding state.

WO97/26010 discloses monoclonal antibodies having self-limiting neutralizing activity against a coagulation factor which are useful in pharmaceutical compositions for thrombotic disorders. Self-limiting neutralizing activity in this document is defined as the activity of an antibody that binds to a human coagulation factor and inhibits thrombosis in a manner such that limited modulation of coagulation is produced. Limited modulation of coagulation in turn is defined as an increase in clotting time as measured by prolongation of the activated partial thromboplastin time (aPTT) where plasma remains clottable with aPTT reaching a maximal value, preferably 35 to 100 seconds, despite increasing concentrations of the monoclonal antibody. APTT is thus used as the primary criterion for the evaluation of efficacy versus bleeding liability of antithrombotic agents.

More particularly, this document demonstrates that a sheep polyclonal to factor VIII (SAF8C-IG, purchased from Affinity Biologicals) induces a self-limiting prolongation of aPTT (the aPTT increased to a maximum of about 65 seconds). We have demonstrated, however, that SAF8C-IG totally inhibits the activity of human factor VIII (see FIG. 10), i.e. is a type I inhibitor in the classification of Gawryl et al., *Blood* (1982) 60: 1103–9. This demonstrates that a limited increase in clotting time up to a certain maximum value is not necessarily correlated with partial inactivation of a clotting factor, and far less to a decrease in the risk of bleeding. For instance, it is well known that patients with a complete deficit of coagulation factors have a limited prolongation of aPTT, usually in the area of 60 to 100 seconds, but are nevertheless exposed to a dramatic risk of bleeding (Hathaway et al. *Am J Clin Pathol* (1979) 71: 22–25, and Hoffmann et al. *Thromb Haemostas* (1978) 39: 640–645).

Conversely, it is well known that a prolonged APTT does not provide a valid parameter of the reduction of thrombosis risk. Notably, deficiency in factor XII, another coagulation factor of the intrinsic coagulation pathway results in APTT prolonged up to 6-fold (Hathaway et al. *Am J Clin Pathol* (1979) 71: 22–25, and; Hoffmann et al. *Thromb Haemostas* (1978) 39: 640–645). However, a significant number of patients with this deficiency have experienced myocardial infarction or thromboembolism, demonstrating the lack of protection from thrombotic disease in patient deficient in factor XII, despite important prolongation of the APTT (McPherson RA *Am J Chin Pathol* (1977) 68: 420, and; Glueck H et al. *Ann Intern Med* (1966) 64:390).

Jacquemin et al. in *Blood* (1998) 92:496–506 refers to a factor VIII-specific human IgG4 monoclonal antibody (BO2C11) produced by a cell line derived from the memory B-cell repertoire of a hemophilia A patient with inhibitors. BO2C11 is said to recognize the C2 domain of factor VIII and to inhibit its binding to both von Willebrand factor and phospholipids. It is said to completely inhibit the procoagulant activity of native and activated factor VIII with a specific activity of 7,000 Bethesda units/mg. The present inventors have further-shown that BO2C11, while totally inhibiting the activity of human factor VIII, provides a prolongation of about 110 seconds in clotting time as measured by aPTT, which again demonstrates that an increase in clotting time up to a certain maximum value is not necessarily correlated to partial inactivation of a coagulation factor. Such a reduction of factor VIII levels would expose the patient to severe risks of bleeding, like in patients with severe hemophilia A (Levine PH *Ann NY Acad Sci* (1975) 240:201; Gilbert MS *Mount Sinai J Med* (1977) 44: 339).

SUMMARY OF THE INVENTION

The present invention is related to new ligands, namely new monoclonal human or humanized antibodies, fragments, derivatives and homologs thereof, which bind to a factor involved in hemostasis, in particular to a factor or factors of the coagulation cascade and more in particular bind to factor VIII or a complex thereof; to polypeptides or other molecules which bind to a factor or factors in hemostasis; to a novel cell line from which said monoclonal antibodies may be obtained; to pharmaceutical compositions comprising said ligands and to methods of prevention and treatment of coagulation disorders and resulting thrombotic pathologic conditions in humans by the administration of said ligands to patients in need thereof.

A first main object of the present invention is therefore to provide an effective and safe anti-thrombotic therapy which reduces the risk of bleeding in mammals, more particularly in humans.

It is a further object of this invention to provide therapeutic compositions which provide an effective anti-thrombotic therapy which reduces the risk of bleeding in mammals, more particularly in humans.

It is still a further object of the present invention to provide an anti-thrombotic therapy and anti-thrombotic therapeutic compounds which are safer to use than the previously known therapies and compositions.

One aspect of the present invention is to target a human protein factor involved in hemostasis, in particular in the coagulation cascade, more particularly factor VIII or a complex thereof, using specific ligands. Preferably, these ligands, being other than polyclonal antibodies, provide a therapeutically useful plateau level by only partially inhibiting the function of the targeted factor so that a residual activity of the factor remains even when the ligand is used in a molar excess. A curve may be established of the inhibiting effect of a ligand in accordance with the present invention with respect to a certain targeted factor against the concentration of the said ligand and the concentration may be determined at which a minimal residual factor activity still exists which is at least 1%, preferably at least 2%. The residual factor activity at five times this concentration should not be substantially different from the residual activity at the minimal point. It is especially a further aspect of the present invention to provide high affinity monoclonal antibodies, both human and humanized, as well as fragments, derivatives, and homologs of any of these, having the capacity to only partially inactivate a factor or factors in hemostasis, in particular in the coagulation cascade and more in particular factor VIII or a complex thereof, even in molar excess of the ligand, thereby preventing the risk of overdosage and the resulting bleeding complications. It is still another aspect of the present invention to provide a novel cell line producing the respective human monoclonal antibody.

The present invention also includes polynucleotide sequences which encode for the antibodies or fragments thereof mentioned above. It will be appreciated that a multitude of nucleotide sequences exist which fall under the scope of the present invention as a result of the redundancy in the genetic code. The present invention also includes complementary sequences which correspond to the monoclonal antibodies, or fragments thereof, mentioned above. In particular, the present invention includes probes constructed from the monoclonal antibodies, or fragments thereof, mentioned above or from the polynucleotides or from the complementary sequences mentioned above.

The present invention further provides a method of attenuation of coagulation in humans, comprising administering a ligand, being other than a polyclonal antibody, such as a monoclonal antibody, either human or humanized, fragment, derivative or homolog thereof, capable of only partially inactivating a factor or factors in hemostasis, in particular in the coagulation cascade and more in particular factor VIII or a complex thereof to a patient in need of such attenuation even when the said ligand is in a molar excess. It further provides a method of treatment or prevention of a thrombotic pathologic condition in mammals, namely in humans, comprising administering a therapeutically effective amount of a ligand, other than a polyclonal antibody, for instance a monoclonal antibody, either human or humanized, or a fragment, derivative or homolog thereof, capable of only partially inactivating, even when the said ligand is in a molar excess, a factor or factors involved in hemostasis, in particular in the coagulation cascade, and more particularly factor VIII or a complex including factor VIII, to a mammal in need of such treatment or prevention. In a preferred embodiment, the thrombotic pathologic condition may be selected for instance from intravascular coagulation, arterial thrombosis, arterial restenosis, venous thrombosis and arteriosclerosis.

Another embodiment of the present invention is directed to a pharmaceutical composition comprising a ligand, other than a polyclonal antibody, having the capacity of binding to a site on a factor or factors involved in hemostasis, in particular in the coagulation cascade, and more particularly factor VIII or a complex including factor VIII, for only partially inactivating the said factor or factor complex even when the ligand is in molar excess, in admixture with a pharmaceutically acceptable carrier. The said ligand preferably is a high affinity anti-factor VIII or anti-factor VIII-von Willebrand factor complex monoclonal antibody, either human or humanized, or hybridized, or a fragment, derivative or homolog thereof. The pharmaceutical composition of the present invention may further optionally comprise a therapeutically effective amount of a thrombolytic agent.

Another embodiment of the present invention is directed to methods for the selection of specific monoclonal antibodies. The conventional technique of immunizing an animal such as a mouse with a protein such as factor VIII elicits an immunological response which may involve several epitopes on the factor VII molecule. The present invention provides more selective methods of obtaining specific monoclonal antibodies against an epitope of a wild-type protein. First, a donor, e.g. a mammal such as a human, is provided (i.e. selected) which has an at least partially functional modified version of a wild-type protein. The said modification, which lies in a domain of the protein, may be due to any cause, e.g. race or variety, to genetic defects at birth, to an illness or by human interference, e.g. immunotolerance against the functionally modified version. The mammal donor is then administered the wild-type protein in order to elicit an immune response; at this stage, it is important that a sufficient quantity of the wild-type protein (e.g. factor VIII) be administered until an immune response is generated. Then, in a final step of the method, selection of B-cells from the mammal donor will result in a much greater chance of obtaining monoclonal antibodies against an epitope in the region of the modification, for instance by selecting B-lymphocytes from the donor which produce antibodies only partially inactivating the wild type protein.

The anticoagulant potential of inhibiting factor VIII has to date not been explored, perhaps because of the well known bleeding complications that occur in hemophilia A patients that lack factor VIII activity completely (severe hemophilia) or to a large extent (moderate hemophilia). Hemophilia A, however, not only demonstrates the importance of factor VIII as limiting co-factor of coagulation, but also the existing link between coagulation and the development of atherosclerosis. Atherosclerosis and its thrombotic complications were indeed found to be significantly rarer among patients with hemophilia A. Antagonizing factor VIII activity at a level that allows sufficient hemostasis to prevent bleeding but protects from pathologic intravascular thrombus formation therefore holds substantial promise for safe anticoagulation in prothrombotic diseases such as deep vein thrombosis (DVT), pulmonary embolism (PE), postoperatively, in pregnancy, in coronary artery disease (CAD), cerebrovascular disease (CVD), peripheral artery disease (PAD) and in vascular interventions.

The present invention is based on on the surprising determination of new ligands, namely new human and humanized monoclonal antibodies and fragments, derivatives and homologs thereof. These may exhibit an unforeseen "plateau effect", i.e. the achievement of only a partial inactivation of a factor involved in hemostasis, in particular in the coagulation cascade, either individually or in combination, whatever the excess of ligand. The ligands may bind to a factor or a complex of factors resulting in only partially impairing the function of a physiologically functional site of the said factor or factor complex. This "plateau effect" makes the ligands particularly suitable for treating coagulation disorders and resulting thrombotic pathologic conditions while minimizing the risk of bleeding, by comparison, notably, to antibodies with self-limiting neutralizing activity mentioned in WO97/26010. There is therefore a sharp contrast between the "the self-limiting neutralizing activity of antibodies to coagulation factors disclosed in WO97/26010 and the clinically meaningful plateau inhibition that the present invention covers, where anti-factor VIII antibodies such as KRIX-1 inhibit factor VIII activity by no more than 85%.

Particularly useful is a property of ligands in accordance with the present invention to allow some physiological function of the affected site even when the ligand is in molar excess. The ligands may be anti-factor VIII antibodies or antibodies against a factor VIII complex, in particular human or human hybrid monoclonal antibodies which bind to factor VIII or a factor VIII complex and at least partially inhibit the activity of factor VIII. Data indicate that type II inhibitors react with different antigenic determinants than type I antibodies and that these determinants are partially blocked in the factor VIII/von Willebrand factor complex.

The present invention will now be described in more details with reference to the following drawings.

BRIEF DESCRIPTION OF THE DRAWINGS

FIGS. 6 and 8 show amino acid sequences (SEQ ID NO:2 and SEQ ID NO:8,) (the lower lines) and nucleotide sequences (SEQ ID NO:5 and SEQ ID NO:7) (upper lines) for the variable regions $V_H$ of the heavy chains of BO2C11 and the KRIX 1 monoclonal antibodies, respectively. Also shown are the three complementarity determining regions (CDR) of each claim which are each an individual polypeptide ligand in accordance with an individual embodiment of the present invention.

FIGS. 7 and 9 show amino acid sequences (SEQ ID NO:3 and SEQ ID NO:1) (the lower lines) and nucleotide sequences (SEQ ID NO:6 and SEQ ID NO:4) (upper lines) for the variable regions $V_L$ of the light chains of BO2C11 and the KRIX 1 monoclonal antibodies, respectively. Also shown are the three CDR's of each chain which are each an individual polypeptide ligand in accordance with an individual embodiment of the present invention.

DEFINITIONS

Figure 1:
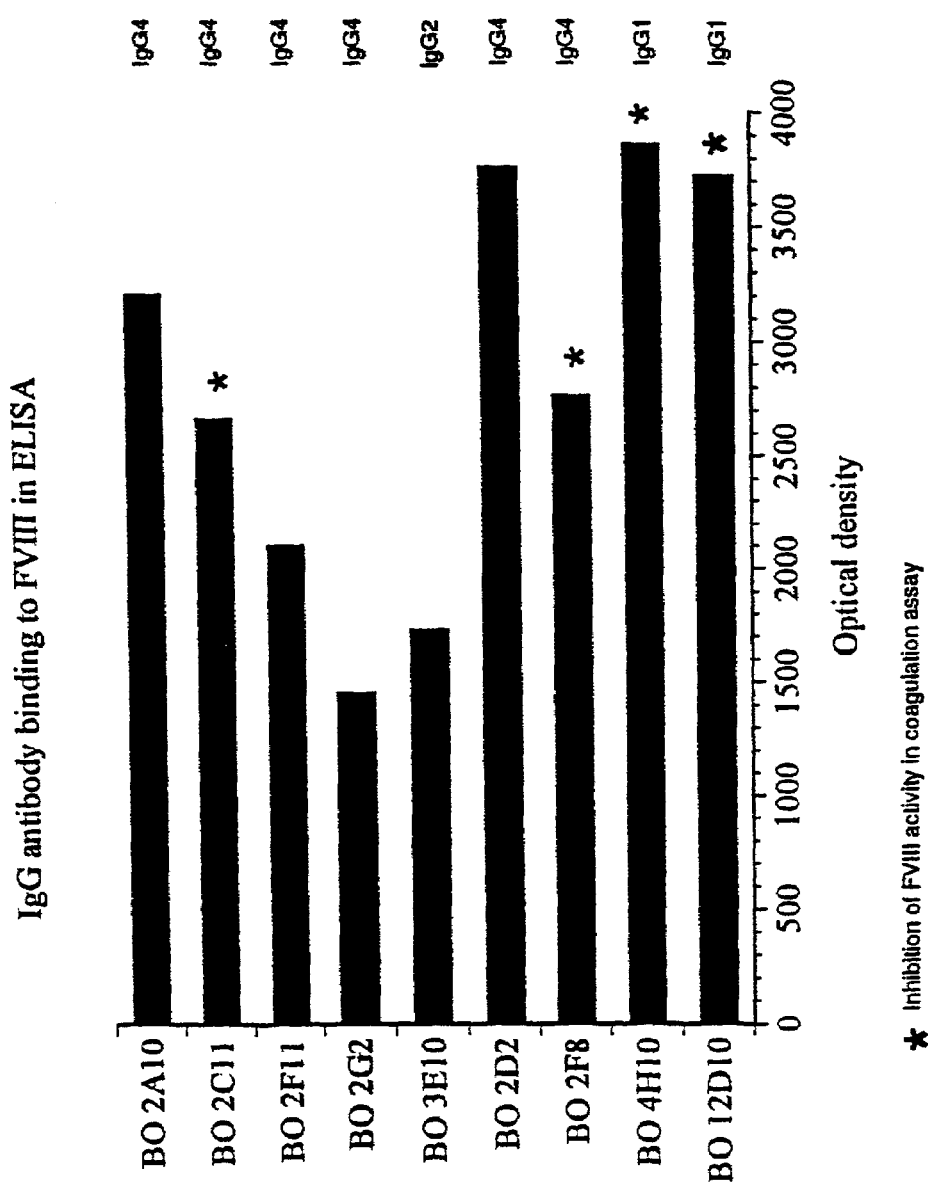
FIG. 1 presents the results of producing human monoclonal antibodies derived from a hemophilia A patient, expressed in the form of IgG antibody binding to factor VIII in ELISA.

The term "antibody" refers to intact molecules as well as fragments thereof, such as Fab, Fab', F(ab')$_2$ or Fv, which are capable of binding to the epitope determinant of the relevant factor or domain of the factor.

"Humanized antibody" as used herein, refers to antibody molecules in which amino acids have been replaced in the non-antigen binding regions in order to more closely resemble a human antibody.

A "Reshaped human antibody" or a "Human hybrid antibody" as used herein, refers to a human antibody in which amino acids in the antigen binding regions have been replaced with sequences in accordance with the present invention, e.g. CDR's, or other parts of variable regions which have been derived from the repertoire of human antibodies.

The term "homology" or "homologous" as used herein with reference to ligands in accordance with the present invention refers to a molecule which will compete with or inhibit binding of one of the ligands in accordance with the present invention to the target site. The binding should be specific, i.e. the binding of the alternative molecule should be as specific to the site as the ligand in accordance with the present invention. Where the ligands in accordance with the present invention include amino acid sequences, homology may include having at least 80%, more preferably 90% and most preferably 95% amino acid sequence identity with the relevant ligand.

DETAILED DESCRIPTION OF THE INVENTION

The present invention will be described with reference to certain embodiments and to certain figures but the present invention is not limited thereto but only by the claims. In particular, the present invention will mainly be described with reference to ligands to factor VIII but the present invention is not limited thereto. The present invention relates to a general concept of obtaining a therapeutically useful "plateau inhibition" by only partially inactivating a factor in hemostasis by the selection of certain monoclonal antibodies, as well as producing such human or humanized monoclonal antibodies, or fragments, derivatives or homologs thereof, and using these for anti-thrombotic therapy and in anti-thrombotic therapeutic compositions. These ligands and compositions may have the advantageous property that the inactivation of the factor is only partial even when the ligand is in a molar excess. This means that even though the ligand is used in an amount which might be expected to inactivate completely the targeted factor, the inactivation is still incomplete.

The present invention provides a particular cell line producing human monoclonal antibodies which are reactive with human factor VIII and more specifically have the capacity of inactivating the co-factor activity of human factor VIII by interfering with proteolytic cleavage site or von Willebrand factor or tenase complex reaction or by inducing a three-dimensional conformational change in factor VIII, in particular by targeting a domain of factor VIII and by recognizing epitopes located in the said domain. One preferred domain is the C1 domain of factor VIII but the present invention is not limited thereto. A site on the C2 domain of factor VIII may also be partially inhibited. The present invention also includes ligands other than polyclonal antibodies, in particular monoclonal antibodies, which reduce the release rate of factor VIII from von Willebrand factor. These monoclonal antibodies specifically target factor VIII when bound to von Willebrand factor and hence target an epitope associated with the complex of factor VIII and von Willebrand factor. The present invention also provides fragments of any of the above monoclonal antibodies such as Fab, Fab', F(ab')$_2$, scFv, CDR's, single variable domains as well as derivatives, homologs and combinations of these. More particularly, these monoclonal antibodies and fragments may target a domain of factor VIII, in particular the C1 domain of factor VIII. They may also partially inhibit a site on the C2 domain of factor VIII. They may also target an epitope associated with the complex of von Willebrand factor and factor VIII. An aspect of the present invention is therefore to provide ligands other than polyclonal antibodies which bind to a first site (e.g. in the C1 domain of factor VIII) remote from a functional second site (e.g. the site in the C2 domain of factor VIII which is responsible for binding phospholipids) in such a way that the function of the second site is only partially impaired even when the ligand is in a molar and therapeutic excess.

The cell line named KRIX 1 producing monoclonal antibodies according to the present invention was deposited with the BCCM/LMBP (Belgian Co-ordinated Collections of Microorganisms/Plasmid Collection Laboratorium voor Moleculaire Biologie, University of Ghent K.L. Ledeganckstraat 35, B-9000 Ghent, BE under accession number LMBP 5089CB on Jul. 1, 1999.

The present invention further provides cell lines producing human monoclonal antibodies having a reactivity substantially similar to that of the human monoclonal antibodies obtained from the above-mentioned deposited cell line, as well as the human monoclonal antibodies obtainable from these further cell lines.

The present invention further provides reshaped human monoclonal antibodies or human hybrid monoclonal antibodies against factor VIII, which bind to and only partially inactivate factor VIII or a complex including factor VIII and von Willebrand factor which comprise only elements derived from the repertoire of human antibodies. By human hybrid monoclonal antibodies it is meant a hybrid antibody constructed from a human antibody and from variable regions in accordance with the present invention. Conventionally in the art, until now it has only been possible to obtain antibodies against factor VIII derived from animals, e.g. mice, or to construct chimeric antibodies from human antibodies with the variable portions derived from mice antibodies.

The present invention also provides ligands, other than polyclonal antibodies, having the capacity of only partially inactivating a factor (or a complex including a factor) involved in hemostasis, in particular in the coagulation cascade of blood, preferably factor VIII or a complex including factor VIII, by binding to a site of the said factor or complex, the said only partial inactivation also taking place when the ligand of the invention is in a molar excess with respect to the said factor. The site to which the ligand binds may or may not be directly or substantially involved in a physiological interaction of the said factor or complex. For instance, the ligand may bind to a site which is at a predetermined distance away from a physiologically functional site of the said factor. By partial "plateau" inactivation, herein we mean an at most 98% inactivation, preferably an at most 95% inactivation, as determined by a suitable test method such as for instance the chromogenic assay available from Coatest® (Kabi Vitrum, Brussels, Belgium) or from Chromogenix AB, Mölndal (Sweden). The level of activation required may depend upon the physiological function of the factor involved in hemostasis. On the other hand, in order to provide therapeutic usefulness, inactivation of the blood factor should be at least about 65%, preferably at least about 70%, as determined by the same test method as above. It will be appreciated that the ligands in accordance with the present invention operate in a different way from the mechanism conventionally ascribed to type II antibodies against factor VIII. One conventional mechanism is that of competition with another factor, e.g. von Willebrand factor. The kinetics of a competition mechanism mean that if the one species is at a high concentration compared with the other (e.g. in a molar excess), the inhibition is effectively complete. In contrast, the ligands of the present invention reach a plateau in the inactivation of the relevant factor, which is substantially independent of the excess of the ligand. The other conventional mechanism ascribed to type II antibodies is that of low affinity: also in this case, an excess will drive the reaction to complete inhibition.

When the targeted blood factor is factor VIII, the ligands of the invention may be human monoclonal antibodies obtainable from the deposited cell line KRIX 1, preferably being of class IgG, and which have the capacity of only partially inactivating the co-factor activity of factor VIII. More specifically the invention relates, in a preferred embodiment, to human monoclonal antibodies from such origin which are able to recognize epitopes located in the C1 domain of factor VIII. Although the inventors do not wish to be bound to a single explanation or theory, it is believed that the binding of such human monoclonal antibodies results in partial impairment of the binding of activated factor VIII to phospholipids, a necessary step for cofactor activity expression.

The present invention further provides monoclonal antibodies having substantially the same characteristics as above disclosed and being produced by on purpose immunization in animals, preferably in mouse, for instance by injecting human factor VIII in mice and then fusing the spleen lymphocytes with a mouse myeloma cell line, followed by identifying and cloning the cell cultures producing anti-factor VIII antibodies. The monoclonal antibodies produced in animals are then humanized, for instance by associating the binding complementarity determining region ("CDR") from the non-human monoclonal antibody with human framework regions—in particular the constant C region of human gene—such as disclosed by Jones et al. in *Nature* (1986) 321:522 or Riechmann in *Nature* (1988) 332:323.

The present invention also provides fragments and derivatives, in particular complementarity determining regions ("CDR's") of the above monoclonal anti-factor VIII antibodies as well as homologs thereof. For instance, the invention provides antigen-binding fragments Fab, Fab' and F(ab')$_2$ generated by proteolytic digestion of the said monoclonal antibodies using methods well known in the art, such as described by Stanworth et al., *Handbook of Experimental Immunology* (1978), vol. 1 chapter 8 (Blackwell Scientific Publications). Such fragments, which contain the antibody binding site, have lost a number of properties of the parent antibody, such as complement activation or capacity to bind to Fc gamma receptors. The present invention also includes single chain fragment variables (scFv), single variable domain fragments of the antibodies and combination of these fragments and of the above mentioned fragments.

The invention also provides soluble or membrane anchored single-chain variable parts of the above monoclonal antibodies and a method for their obtention as follows. The DNA sequences of the variable parts of human heavy and light chains are amplified in separated reactions and cloned. A fifteen ammo-acid linker sequence, for instance (Gly4 Ser)3, is inserted between VH and VL by a two-steps polymerase chain reaction (PCR), for instance according to Dieffenbach and Dveksler, "PCR Primer, a laboratory manual" (1995), Cold Spring Harbour Press, Plainview, N.Y., USA. The resulting fragment is then inserted into a suitable vector for expression of single chain fragment variable (scFv) as soluble or phage-displayed polypeptide. This can be achieved by methods well known to those skilled in the art, such as described by Gilliland et al., Tissue Antigens (1996) 47:1–20. The present invention also includes a ligand comprising peptides representative of hypervariable regions of a monoclonal antibody which can be obtained by synthesis using an applied biosystem synthesizer, for instance a polypeptide synthesizer such as model 9050 available from Milligen (USA) or a model from a related technology, which alone or in combination with other or similar hypervariable regions will exert properties similar to that of the parent antibody.

The invention further provides a pharmaceutical composition for the prevention or treatment of disorders of hemostasis, in particular of the coagulation cascade and resulting thrombotic pathologic conditions in humans, comprising, as an active ingredient, a ligand other than a polyclonal antibody, preferably a human monoclonal antibody such as disclosed hereinabove, in admixture with a pharmaceutically acceptable carrier. More preferably the said monoclonal antibody is a human monoclonal antibody, or a fragment, derivative or homolog thereof, obtainable from the cell line KRIX 1 deposited with the Belgian Co-ordinated Collections of Micro-organisms under accession number LMBP 5089CB. The degree of homology with the said monoclonal antibody is preferably at least 80%, more preferably 90% and most preferably 95%, and the homology is preferably particularly in respect to the complementarity determining regions of the antibody. A ligand in accordance with the present invention may also include a synthetic polypeptide of equivalent potency. The pharmaceutical composition of the present invention should comprise a therapeutically effective amount of the said above ingredient, such as indicated hereinafter in respect to the method of treatment or prevention.

The pharmaceutical composition of the present invention may further comprise, namely in view of a so-called adjunctive anti-thrombotic treatment, a therapeutically effective amount of a thrombolytic agent. Such thrombolytic agents, as well as their usual dosage depending on the class to which they belong, are well known to those skilled in the art. Among numerous examples of thrombolytic agents which may be included in the pharmaceutical compositions of the invention, the following non-limiting list may be particularly cited: t-PA, streptokinase, reptilase, TNK-t-PA or staphylokinase.

Suitable pharmaceutical carriers for use in the pharmaceutical compositions of the invention are described for instance in Remington's Pharmaceutical Sciences 16$^{th}$ ed. (1980) and their formulation is well known to those skilled in the art. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the monoclonal antibody active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the monoclonal antibody active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition comprising the active ingredient may require protective coatings. The pharmaceutical form suitable for injectionable use include sterile aqueous solutions or dispersions and sterile powders for the extemporaneous preparation thereof. Typical carriers therefore include biocompatible aqueous buffers, ethanol, glycerol, propylene glycol, polyethylene glycol and mixtures thereof.

The present invention also provides the use of a ligand, other than a polyclonal antibody (as disclosed above) as a medicament. More preferably the medicament used in the present invention is a means for preventing and/or treating disorders of hemostasis, in particular, coagulation disorders and other thrombotic pathologic conditions in mammals, preferably in humans. The said ligand may be provided to a patient by any means well known in the art, i.e. orally, intranasally, subcutaneously, intramuscularly, intradermally, intravenously, intraarterially, parenterally or by catheterization. According to the present invention, the ligand may also be used as a medicament in conjunction or association with another medicament, for instance a thrombolytic agent such as disclosed hereinabove under the heading of pharmaceutical compositions.

The present invention therefore provides a method of treatment and/or prevention of hemostasis, coagulation disorder or thrombotic pathologic condition as well as a method of attenuation of coagulation in a mammal, preferably a human, comprising administering to a mammal in need of such treatment or prevention or attenuation of coagulation a therapeutically effective amount of a ligand other than a polyclonal antibody such as disclosed hereinabove. Preferably the said ligand is a human or humanized monoclonal antibody obtainable from cell line KRIX 1 deposited with the Belgian Co-ordinated Collections of Micro-organisms under accession number LMBP 5089CB or an antigen-binding fragment Fab, Fab' or F(ab')$_2$, a complementarity determining region (CDR), a soluble or membrane-anchored single-chain variable part (scFv), a single variable domain or a derivative or combination of any of these elements.

A therapeutically effective amount as used herein means from about 1 microgram to about 10 milligrams per kilogram of body weight, more preferably from about 10 micrograms to about 1 milligram per kilogram of body weight of the mammal to be treated. It will be appreciated that, in view of the long half-life time of most IgG human antibodies, the ligands of the present invention which are monoclonal antibodies of the said class will enjoy a periodicity of treatment which participates in the comfort of the patient.

As preferred embodiments of the said thrombotic pathologic condition to be prevented or treated, may be cited intravascular coagulation, arterial thrombosis (which may be responsible for acute myocardial infarction and stroke), arterial restenosis, venous thrombosis (which commonly occurs in peripheral veins as a consequence of accidental or surgical trauma or immobilization) or arteriosclerosis. In a most preferred method of treatment, the patient is provided with a bolus (intravenously injected) at a dosage determined by the ordinary skilled physician depending on criteria which establish the particular patient's clinical condition.

The method of treatment and/or prevention according to the invention may include further treatment or prevention of the same thrombotic pathologic condition by administrating, preferably by sequentially administrating, to the patient a therapeutically effective amount of a thrombolytic agent such as disclosed hereinabove under the heading of pharmaceutical compositions. Sequentially, as used herein, means that the ligand of the present invention and the known thrombolytic agent are administered to the patient sequentially but not simultaneously.

The present invention further provides a method of obtaining monoclonal antibodies from a non-human mammal, comprising the steps of:

a) selecting a non-human mammal having a modified and at least partially functional physiologically active protein, the modification being with respect to a wild type protein and lying in a domain of the protein;

b) administering the wild type protein to the non-human mammal in order to elicit an immune response, and c) selecting B-lymphocytes from the non-human mammal which produce antibodies which only partially inactivate the wild type protein.

According to this method, the standard practice is to sacrifice the non-human mammal and to remove its spleen in order to perform step (c).

The present invention additionally provides a method of obtaining monoclonal antibodies from the blood of a human being having a modified and at least partially functional physiologically active protein, the modification being with respect to a wild type protein and lying in a domain of the protein, and to whom the wild type protein was administered, the said method comprising the step of selecting, from the blood of said human being, B-lymphocytes which produce antibodies which only partially inactivate the wild type protein.

The present invention, as embodied in the various above disclosed aspects, has a number of advantages. The major advantage of the therapeutic use of the human monoclonal antibodies of the invention is that the treatment is highly specific for the immune response under consideration. In hypercoagulation states, the specificity of the human monoclonal antibodies of the invention ensures that interaction within the coagulation cascade pathway is limited to the factor recognized by the antibody.

More specifically, the use of the anti-factor VIII antibodies having the above-mentioned preferred characteristics brings a unique combination of the advantages related to the targeting of factor VIII, those related to the characteristics of factor VIII inhibition and those related to the use of antibodies:

targeting factor VIII means that neutralizing a co-factor activity such as that of factor VIII caries no risk of completely inhibiting the enzymatic activity it enhances, thereby representing an advantage over methods targeting directly enzymes such as factor IX.

the embodiments of the inhibitors described above have in common that they efficiently but only partially inhibit the co-factor activity of factor VIII, setting a therapeutically useful plateau, even when the monoclonal antibody of the invention is used in more than 100-fold excess. Monoclonal antibodies in accordance with the present invention achieve a plateau effect in inactivation of factor VIII, allowing bolus application, yielding safe antithrombotic protection over several weeks without the need of monitoring or the risk of overdosage.

human IgG antibodies exhibit a prolonged half-life time of three weeks (except for IgG3 which is one week), thus providing very stable plasma levels of the anti-thrombotic agent and allowing for a drastic reduction in the frequency of administration. Further, the use of human antibodies or derivatives carries a minimal risk of inducing immune responses.

The present invention is further described by the following examples which are provided for illustrative purposes only.

EXAMPLE 1

Production of Monoclonal Antibodies Derived from Hemophilia A Patients

Human monoclonal antibodies of the desired specificity and characteristics are produced by transformation of B lymphocytes obtained from the peripheral blood of patients suffering from hemophilia A or acquired hemophilia. The method of selecting patients is an embodiment of the present invention. In order to elicit a more specific immunological response, patients are sought who have an impaired function of a physiologically active protein, e.g. factor VIII. By "impaired" is meant that some residual function is available but that this is less than is known for the wild-type of the same protein. A comparison between the self-protein and the wild-type protein should exhibit a difference in the two proteins, preferably in a region or domain which is of interest. The difference may be a deletion or a substitution of one or more amino acids with others. The patients are then administered enough of the wild-type protein to elicit an immunological response. Then, B-lymphocytes are extracted from the patients and selected based on the production of antibodies which have desirable properties. Although reference is made to "patients" above, the method in accordance with this embodiment may be applied generally to mammals. The above procedure results in a greater chance of obtaining antibodies which target the domain containing the defect.

B cells are transformed by infection with the Epstein-Barr virus and activation of surface antigens using techniques well known by those skilled in the art. Cell supernatants containing appropriate antibodies are identified by a specific assay procedure such as described in more details hereinbelow.

Thus, antibodies towards factor VIII are identified by reacting the supernatant with polystyrene microtitration plates coated with factor VIII or with factor VIII/von Willebrand factor complexes. The binding of specific antibodies is detected by addition of a non human IgG reagent coupled to an enzyme. Addition of an enzyme substrate which is converted to a colored compound in the presence of the enzyme allows the detection of specific antibodies. Such methods referred to as enzyme-linked immunoassays (ELISA) are well known to those skilled in the art and described in details e.g. in *Current Protocols in Immunology*, chapter 2, John Wiley & Sons (1994), the content of which is incorporated herein by reference.

More specifically in the present case, the binding of anti-factor VIII IgG antibodies was detected by addition of a horseradish peroxidase labeled mouse monoclonal antibody specific for human Fc gamma. The IgG subclass of the anti-factor VIII antibody was detected in ELISA, as presented in FIG. 1. The inhibition of factor VIII functional activity was tested in a functional coagulation assay as follows. Equal volume of cell culture supernatant and of a pool of normal plasma were incubated for two hours at 37° C. and the residual factor VIII activity measured thereafter. Those antibodies which significantly inhibit factor VIII activity are shown with an asterisk in FIG. 1.

B cells (such as BO 2C11) producing anti-factor VIII antibodies are then expanded and cloned by limiting dilution as described for instance in *Current Protocols in Immunology* (see supra). Anti-factor VIII antibodies having the capacity to inhibit the procoagulant activity of factor VIII as described above are identified using a chromogenic assay kit such as a factor VIII chromogenic assay assay from Dade, Düchingen, Germany or Coatest® commercially available from Kabi Vitrum (Brussels, Belgium) or Chromogenix AB (Mölndal, Sweden).

Figure 2:
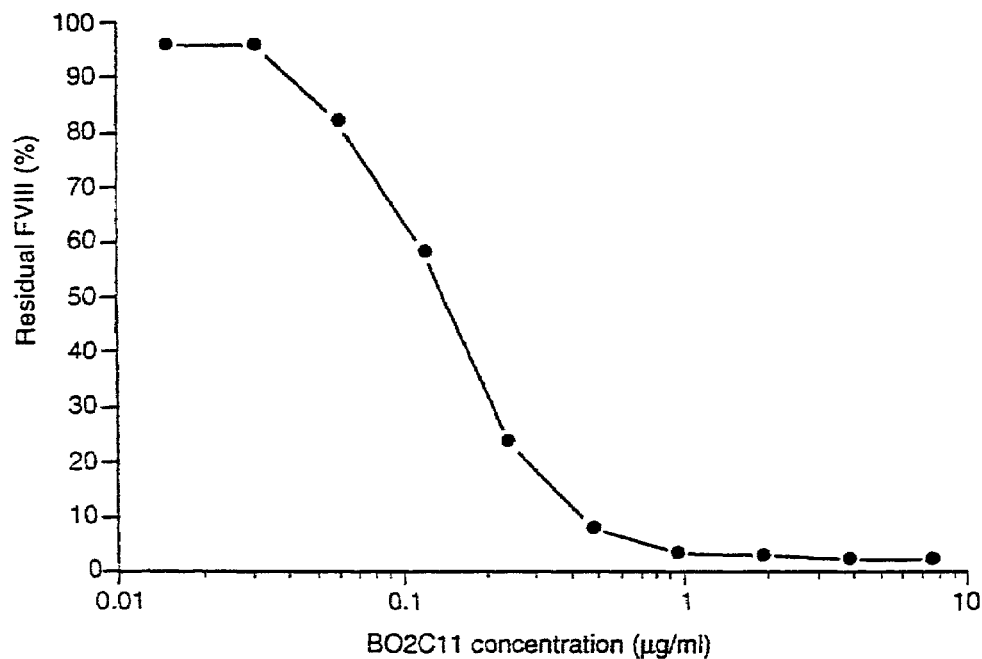
FIG. 2 shows inhibition of factor VIII activity by the monoclonal antibody BO2C11.

Equal volumes of monoclonal antibodies BO 2C11 and a pool of normal blood plasma were incubated for 2 hours at 37° C. BO 2C11 concentrations before mixing are shown on the X axis. The reduction of factor VIII activity was measured in a coagulation assay and was expressed as a percentage of the activity obtained in the absence of antibody (see FIG. 2). The residual activity goes to zero asymptotically (complete inhibition).

Figure 3:
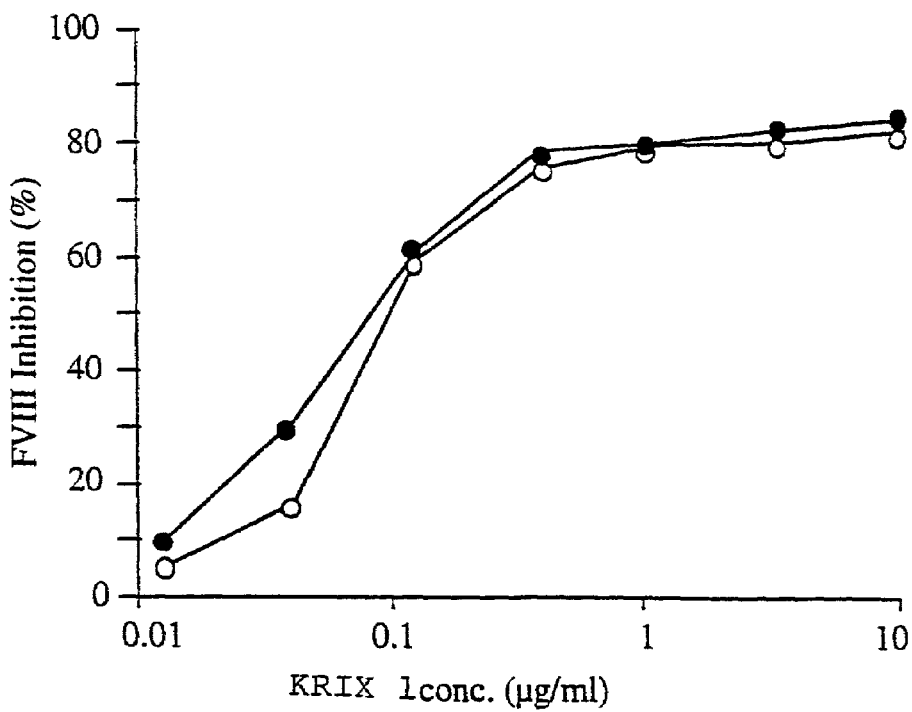
FIG. 3 shows inhibition of factor VIII activity by the monoclonal antibody produced from the cell line KRIX 1.
Figure 4:
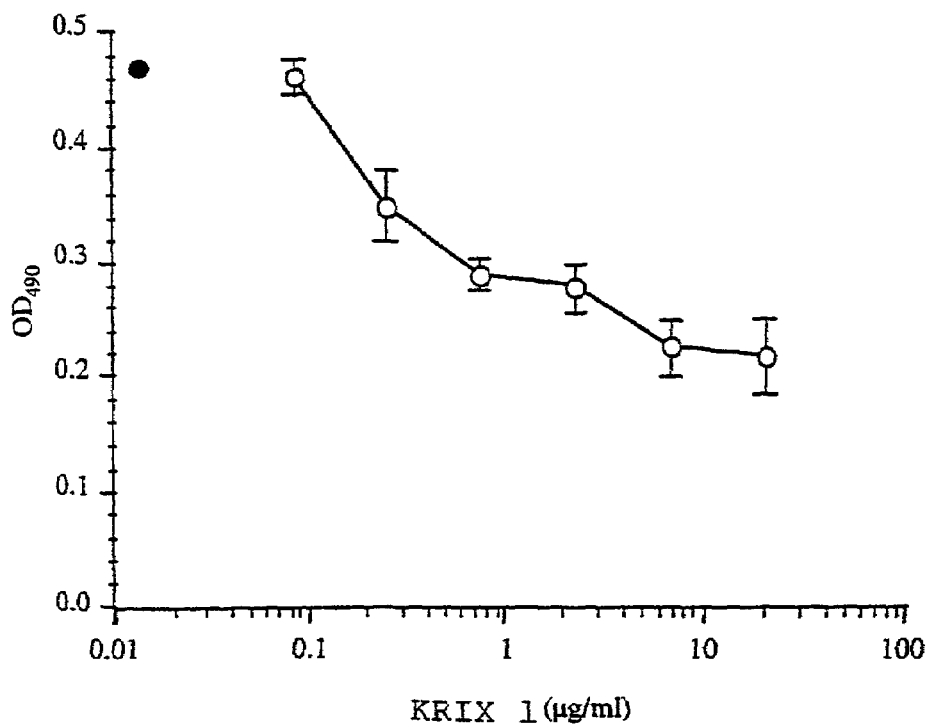
FIG. 4 shows inhibition of the binding of activated factor VIII on phosphatidyl-L-serine by the monoclonal antibody produced from the cell line KRIX 1.

Antibodies which inhibit factor VIII function with sufficient affinity but do not inhibit factor VIII pro-coagulant activity completely, even when used in large antibody excess, were selected in a further embodiment of the present invention. A representative example of such an antibody is provided in FIG. 3 where, equal volumes of KRIX 1 and of recombinant factor VIII or of normal plasma being incubated for two hours at 37° C. and concentrations (expressed in microgr/ml) of KRIX 1 before mixing with plasma being as indicated, the residual factor VIII activity was measured using the above-mentioned chromogenic assay. FIG. 3 interestingly shows about 60% factor VIII inhibition at a concentration of 0.1 microgr/ml and more interestingly an asymptotic factor VIII inhibition of about 80% in the whole range of concentrations from 0.5 to 300 microgr/ml.

The thus selected antibodies are then produced in bulk culture and purified by affinity chromatography using methods well known to those skilled in the art.

The details of a non-limiting preparation technique are as follows. Human recombinant factor VIII (specific activity: 4000 IU/mg) was obtained from Hyland (Glendale, Ca) as material for laboratory use only; plasma-derived (pd) factor VIII-von Willebrand factor complex, purified by ion exchange chromatography (specific activity ±160 IU/mg protein; 15:1 von Willebrand factor to factor VIII w/w ratio), and purified factor VIII-depleted von Willebrand factor (von Willebrand factor to factor VIII w/w ratio 4800:1; lot 951016) were obtained from the Belgian Red Cross (Brussels, Belgium).

Peripheral blood samples were collected from donors suffering mild hemophilia and with inhibitors. The peripheral blood mononuclear cells (PBMC) were immortalized by EBV infection concomitantly to the activation of surface antigens. Four hundred and eighty cell lines were screened by ELISA for production of antibodies towards factor VIII. For example, one cell line, named KRIX 1, was successfully cloned by limiting dilution. Clonality was verified by RT-PCR amplification of mRNA coding for the V regions of the antibody heavy and light chains: a single sequence was obtained from 10 clones of PCR products. Purified antibodies were obtained by passage of KRIX 1 cell culture supernatant on Protein-A Sepharose. An ELISA performed with IgG subclass- and light chain-specific antibodies identified KRIX-1 as an IgG4k.

Human monoclonal antibodies were purified by adsorption on immobilized Protein A (high-TRAP$^R$ Protein A; Pharmacia, Uppsala, Sweden). Fab fragments of human monoclonal antibody were prepared by papain digestion. One mg of a selected antibody was diluted to 500 microgr/ml in phosphate buffer (40 mmol/L $KH_2PO_4$, 60 mM $Na_2HPO_4.2H2O$, 0.15M NaCl) containing 50 mmol/L L-cystein (Sigma), 1 mmol/L EDTA (Merck) and 10 microgr papain (Sigma). The mixture was incubated for 3 h at 37° C. with continuous agitation. The reaction was stopped by addition of iodoacetamide to a final concentration of 75 mmol/L for 30 min at RT. The digested antibody was dialysed against phosphate-buffered saline (140 mmol/L NaCl, 67 mmol/L KCl, 20 mmol/L $Na_2HPO_4$, 4.4 mmol/L $KH_2PO_4$, pH 7.4). The undigested IgG and Fc fragments were then eliminated by passage over protein A sepharose (Hi Trap Protein A; Pharmacia). The Fab fragment was further purified by gel filtration chromatography on a Superdex 200 (Pharmacia).

Conventional methods were used for the detection of anti-factor VIII IgG antibodies, the determination of IgG subclass, and the evaluation of inhibition of factor VIII binding to von Willebrand factor. For the analysis of the inhibition of the binding of rfactor VIII to a selected antibody by Fab and native antibody, Maxisorb polystyrene plates (Nunc) were coated for 2 h with 50 µl of the antibody diluted to 5 microgr/ml in glycine-buffered saline (20 mmol/L glycine, 34 mmol/L NaCl, pH 9.2). After washing, 50 µl of biotin-labeled rfactor VIII diluted to 1 microgr/ml in Tris-casein (10 mmol/L tris(hydroxymethyl)-aminoethane, pH 7.3, containing 150 mmol/L NaCl and 0.5% casein) were mixed for 1 h at 37° C. with 50 µl of human IgG at various dilutions. A 50-µl aliquot of the mixture was added to the plates for 2 h at RT. After washing, the binding of biotinylated rfactor VIII was detected by sequential addition of avidin-peroxydase and OPD.

rfactor VIII (final concentration 0.2 microgr/mL) was incubated with human IgG antibody at different concentrations for 2 hours at 37° C. and the residual factor VIII activity was assessed by a chromogenic assay (Coatest Factor VIII, Chromogenix AB, Mölndal, Sweden or Kabi Vitrum, Brussels, Belgium). Inhibition of plasma factor VIII activity was measured by the Bethesda method, in which a pool of normal plasma collected in buffered trisodium citrate was used as factor VIII source. Residual factor VIII activity was assessed by a chromogenic or by a one-stage clotting assay.

EXAMPLE 2

Production of Monoclonal Antibodies by Immunization in Animals

Alternatively, monoclonal antibodies having the same characteristics as disclosed in example 1 can be produced by on purpose immunization in animals. Thus, mice are injected with human factor VIII in Freund's adjuvant Monoclonal anti-human factor VIII antibodies are then obtained by fusion of spleen lymphocytes with a mouse myeloma cell line. Cell culture supernatants producing anti-factor VIII antibodies are identified and cloned by limiting dilution, using methods described in *Current Protocols in Immunology* (see supra). Further selection of inhibitors having the desired capacity to inhibit the procoagulant activity of factor VIII is carried out as described in example 1.

Monoclonal antibodies produced in mice are then humanized. Thus, sequences of the variable parts of mouse heavy and light chains are aligned with human immunoglobulin variable regions to identify human antibody with the greatest homology in framework regions. The DNA fragment encoding humanized variable regions are then synthesized by a PCR-based CDR (complementarity determining regions) grafting method as described for instance in Sato et al., *Cancer Research* (1993) 53:851–6. The final PCR product coding for the heavy chain variable part of the humanized antibody is digested and subcloned upstream of the human C gamma-1 gene in a first expression plasmid. The humanized light chain variable region of the final construction is inserted upstream of the C kappa gene in a second expression plasmid. The two constructions are then co-transfected into COS cells expression system.

EXAMPLE 3

Characterization of Anti-Factor VIII Antibodies

Monoclonal antibodies of either human (example 1) or animal (example 2) origin are characterized using an assay system by which their capacity to inhibit the binding of factor VIII to phospholipids is evaluated. Thus, polystyrene microtitration plates are coated with phosphatidyl-L-serine. Soluble recombinant factor VIII at 2 microgr/ml final concentration is mixed for 30 minutes at 37° C. with various concentrations of the antibody under evaluation. The mixture is then rapidly activated with thrombin and added to phosphatidyl-L-serine coated plates. The said plates were then incubated for two minutes at 21° C. and the binding of factor VIII was detected by addition of the anti-factor VIII A1 domain mAbF14A2, for two minutes, followed by a two minute incubation with HRP-conjugated goat anti-mouse Fc gamma. Results of this experiment are shown in FIG. 4 for the monoclonal antibody produced from the cell line KRIX 1. On the figure, the average of activated factor VIII binding in the absence (closed symbols) or presence (open symbols) of the antibody, as well as the standard deviation of triplicates are indicated. Controls in the absence of factor VIII gave OD 490 lower than 0.05. FIG. 4 clearly shows that the monoclonal antibody produced from cell line KRIX 1 inhibits significantly the binding of factor VIII to phospholipids but brings about incomplete inhibition even when added in large excess.

To demonstrate that in absence of plasma, KRIX 1 did not recognize the mutated factor VIII light chain of the donor, DNA fragments encoding wild-type and mutated factor VIII light chains were synthesized. The corresponding proteins were expressed in reticulocyte lysates. The correct folding of native and mutated light chains was determined by immunoprecipitation with the human monoclonal antibody BO2C11, which recognizes a conformational epitope within the carboxy-terminal part of the factor VIII light chain. Immunoprecipitation experiments indicated that BO2C11 bound wild-type and Arg2150His light chains, whereas KRIX 1 captured exclusively the wild-type light chain. Prolonged exposure of SDS-PAGE gels to the autoradiography film failed to detect any significant binding of KRIX 1 to the mutated light chain. Control experiments showed no binding to assay reagents other than factor VIII or factor VIII fragments, and preincubation with soluble rfactor VIII prevented the binding to methionine-labeled factor VIII fragments, confirming the binding specificity.

KRIX 1 did not recognize factor VIII in Western blotting indicating that the epitope recognized was conformational. Further epitope mapping was therefore performed with factor VIII fragments produced in reticulocyte lysates. Preliminary experiments had indicated that such an approach was efficient for the synthesis of factor VIII domains. The immunoprecipitation procedure using labeled factor VIII domains produced in reticulocyte lysate was validated by mapping the epitope recognized by the human monoclonal antibody BO2C11. A complete agreement was observed between the binding to factor VIII C2 deletion fragments produced in reticulocyte lysates and the binding to recombinant fragments produced in *E. coli* or COS cells. KRIX 1 bound to full-length light chain, to fragments corresponding to A3C1, C1 C2, and the isolated C1 domain. In contrast, KRIX 1 did not bind to the C1 or C1C2 domains with the substitution Arg2150His, although in a control experiment, the Arg2150His C1C2 domain was bound by BO2C11 like its normal counterpart.

A search was made for other mutations in the light chain which could alter the binding of KRIX 1. As shown in Table I, KRIX 1 inhibited the activity of all mutated factor VIII molecules tested so far, except those carrying the mutation Arg2150His.

TABLE I

Inhibition of factor VIII activity in mild hemophilia A patients' plasma.

| factor VIII mutation | factor VIII activity (IU/ml) | KRIX-1 Inhibition (%) |
|---|---|---|
| Arg1689Leu | 0.04 | >70 |
| Arg1749His | 0.39 | >70 |
| Gly1750Arg | 0.38 | >70 |
| Ala1824Val | 0.16 | >70 |
| Asp1825Gly | 0.17 | >70 |
| His1961Tyr | 0.24 | >70 |
| Arg1966Gln | 0.08 | >70 |
| Met2010Ile | 0.04 | >70 |
| Ser2011Asn | 0.23 | >70 |
| Val2016Ala | 0.05 | >70 |
| Asn2019ser | 0.13 | >70 |
| Leu2052Phe | 0.23 | >70 |
| Asp2074Gly | 0.13 | >70 |
| Thr2086Ile | 0.08 | >70 |
| Ile2098Ser | 0.20 | >70 |
| Phe2101Leu | 0.06 | >70 |
| Asn2129Ser | 0.20 | >70 |
| Arg2150His | 0.03 | 0 |
| Pro2153Gln | 0.02 | 65 |
| Arg2159Leu | 0.16 | >70 |
| Trp2229Cys | 0.02 | >70 |
| Gln2246Arg | 0.08 | >70 |

In the use of KRIX 1 as a medicament to partially inhibit factor VIII mild mutations of factor VIII will not affect the effectiveness of the therapy.

KRIX 1 inhibited the binding of factor VIII to von Willebrand factor in a dose-dependent manner. The concentration of KRLX 1 required to achieve 50% inhibition ($IC_{50}$) of factor VIII binding was 0.25 microgr/mL and more than 95% inhibition was obtained with 20 microgr/mL of KRIX 1. Fab fragments of KRIX 1 also inhibited factor VIII binding to von Willebrand factor. However, on a molar basis 15 times more Fab than native KRIX 1 was required to inhibit 50% of actor binding Willebrand factor. Additional experiments were performed to exclude that the Fab fragments still contained intact or partially digested antibody, SDS-PAGE analysis of the Fab fragments purified by protein A adsorption and gel filtration chromatography showed a single band. The presence of trace amounts of Fc gamma fragments remaining bound to Fab fragments was excluded m ELISA. Wells with insolubilised factor VIII were incubated with native or Fab KRIX 1. Binding of both Fab and native KRIX 1 could be detected by addition of peroxidase-labeled anti-kappa light chain IgG. By contrast, addition of peroxidase-labeled anti-Fc gamma IgG did not reveal any specific binding even when 100 microgr/ml of the Fab preparation were incubated into the wells. By comparison, the addition 0.1 microgr/ml of the native antibody gave rise to a significant binding. In ELISA, a 15-fold higher concentration of Fab than of native antibody was required to inhibit 50% of the binding of biotinylated KRIX 1 onto insolubilised factor VIII, indicating that the Fab KRIX 1 fragment had a lower affinity for factor VIII than the native antibody. Accordingly, the requirement for higher concentrations of KRIX 1 Fab than of native antibody to inhibit factor VIII binding to von Willebrand factor should be attributed to the reduced affinity of KRIX 1 Fab fragments for factor VIII.

To determine whether KRIX 1 was representative of the polyclonal antibodies from the donor, a competitive assay was used. The binding of biotinylated KRIX 1 to insolubilised factor VIII was measured in presence of increasing concentrations of either KRIX 1, polyclonal IgG from the donor, or control polyclonal IgG. IgG from the donor dose-dependently inhibited KRIX 1 binding to factor VIII. The concentration of KRIX 1 and IgG from the donor inhibiting 50% of biotinylated KRIX 1 on factor VIII were of 0.3 microgr/ml and of 170 microgr/ml, respectively, whereas no inhibition was observed with the control IgG.

EXAMPLE 4

Production of Monoclonal Antibodies Derived from Hemophilia A Patients and which Bind to the Factor VIII-von Willebrand Factor Complex.

Figure 5:
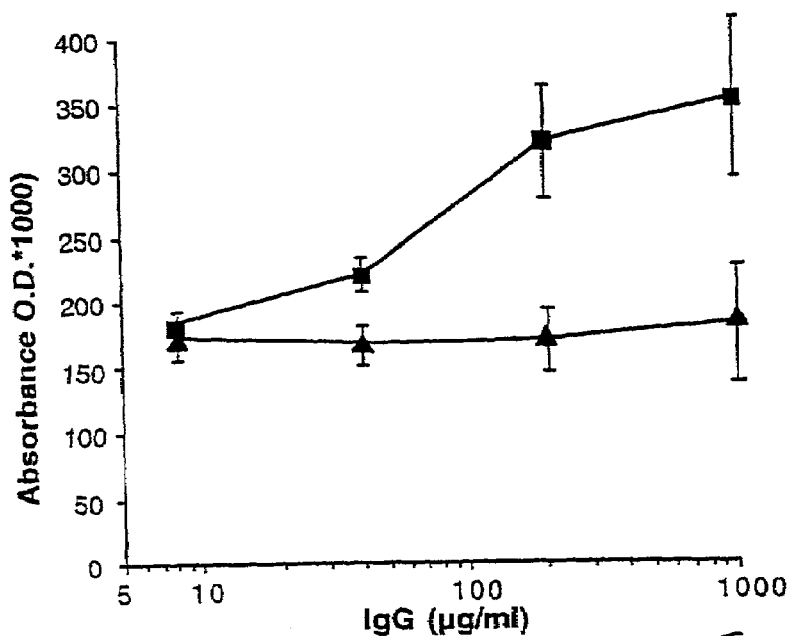
FIG. 5 shows the influence of certain polyclonal antibodies on the dissociation of activated factor VIII from von Willebrand factor.

Alternatively, antibodies which reduce the release rate of factor VIII from von Willebrand factor are identified as follows. Polystyrene microtitration plates are coated with a specific antibody to von Willebrand factor. A solution of biotinylated recombinant factor VIII (0.5 microgr/mL) complexed to von Willebrand factor (5 microgr/mL) is mixed with various concentrations of IgG from a donor (FIG. 5 solid squares), e.g. the same patient as described above (from which KRIX 1 was derived), MoAb4H1D7, or of IgG from a non-hemophiliac subject (FIG. 5 solid triangles). IgG at the indicated concentrations was added to microtitration plates coated with a mouse antibody, MoAb4H1D7 against von Willebrand factor for an incubation of two hours at room temperature. After washing, factor VIII was activated by thrombin during two minutes at 37° C. Factor VIII bound to von Willebrand factor was detected by addition of avidine peroxidase. Controls included the detection of bound biotinylated factor VIII in the absence of thrombin digestion (OD450=460+47.7SD) and of biotinylated recombinant factor VIII after thrombin digestion in the absence of antibody (OD450=160+16.0SD).

Results of these experiments are shown in FIG. 5 for polyclonal antibodies. On this figure, the average values as well as the standard deviation of triplicates are indicated. FIG. 5 clearly shows that a significantly higher proportion of activated factor VIII remains bound to the plate in the presence of increasing concentrations of the antibody, i.e. it demonstrates a reduction of the dissociation of activated factor VIII from von Willebrand factor in the presence of an inhibitor antibody recognizing factor VIII bound to von Willebrand factor. Monoclonal antibodies have been obtained from these polyclonal antibodies in accordance with the methods described in this invention, thus indicating that the present invention may be extended to monoclonal antibodies and fragments and derivatives thereof which bind to Factor VII/von Willebrand factor complexes.

EXAMPLE 5

Sequencing of Antibody Variable Domains

Sequencing of antibody variable domains was carried out as follows. The isolation of RNA from EBV-immortalized human B-cell lines was performed using TRIzol Reagent according to the manufacturer's instructions (Life Technologies). CDNA was synthesized with the SuperScript preamplification system for first-strand cDNA synthesis. The cDNA encoding the heavy chain variable region genes ($V_H$) was amplified by polymerase chain reaction (PCR) using primers specific for the leader sequence of the $V_H$ families and for the first exon of the C gamma region, as described (Bakkus et al, *Blood,* 80:2326, 1992) Annealing was performed at 60° C. for 40 PCR cycles. PCR products of the appropriate size (460 bp) were isolated from 1.5% agarose gel and cloned using the TA Cloning Kit (Invitrogen BV, Leek, The Netherlands). A PCR screening using couples of primers corresponding to the $V_H$ gene family of interest was performed on cultures of randomly selected colonies. Plasmid DNA from positive colonies were isolated using Wizard Plus Minipreps (Promega, Menlo Park, Calif.) and sequenced in both directions with Sequenase (US Biochemical, Cleveland, Ohio), according to the manufacturer's instructions. Analysis of the variable gene sequences was made using the V BASE Sequence Directory (Tomlinson et al, MRC Centre for Protein Engineering, Cambridge, UK).

The complete sequences of the $V_H$ and $V_L$ of the antibody BO 2C11 described in example 1 were submitted to the EMBL Nucleotide Sequence Database under the accession numbers AJ224083 and AJ224084, respectively.

The amino acid sequences shown in FIGS. 6 and 7 define the $V_H$ and $V_L$ regions of the antibody BO2C11 including the three CDR's for each of the heavy and light chains. Also given are the polynucleotide sequences which encode for these regions. SEQ. NOs. 2 and 3 are the amino acid sequences of the heavy and light chains of BO2C11, respectively while SEQ. NOs. 5 and 6 provide the polynucleotide sequences coding for these variable regions.

The amino acid sequences shown in FIGS. 8 and 9 define the $V_H$ and $V_L$ regions of the antibody KRIX-1 including the three CDR's 1–3 for each of the short and long chains. Also given are the polynucleotide sequences which encode for these regions. SEQ. NOs. 8 and 1 are the amino acid sequences of the heavy and light chains of KRIX-1, respectively while SEQ. NOs. 7 and 4 provide the polynucleotide sequences coding for these variable regions.

EXAMPLE 6 (COMPARATIVE)

Inhibition of Factor VIII Activity by the Antibody SAF8C-Ig.

Figure 10:
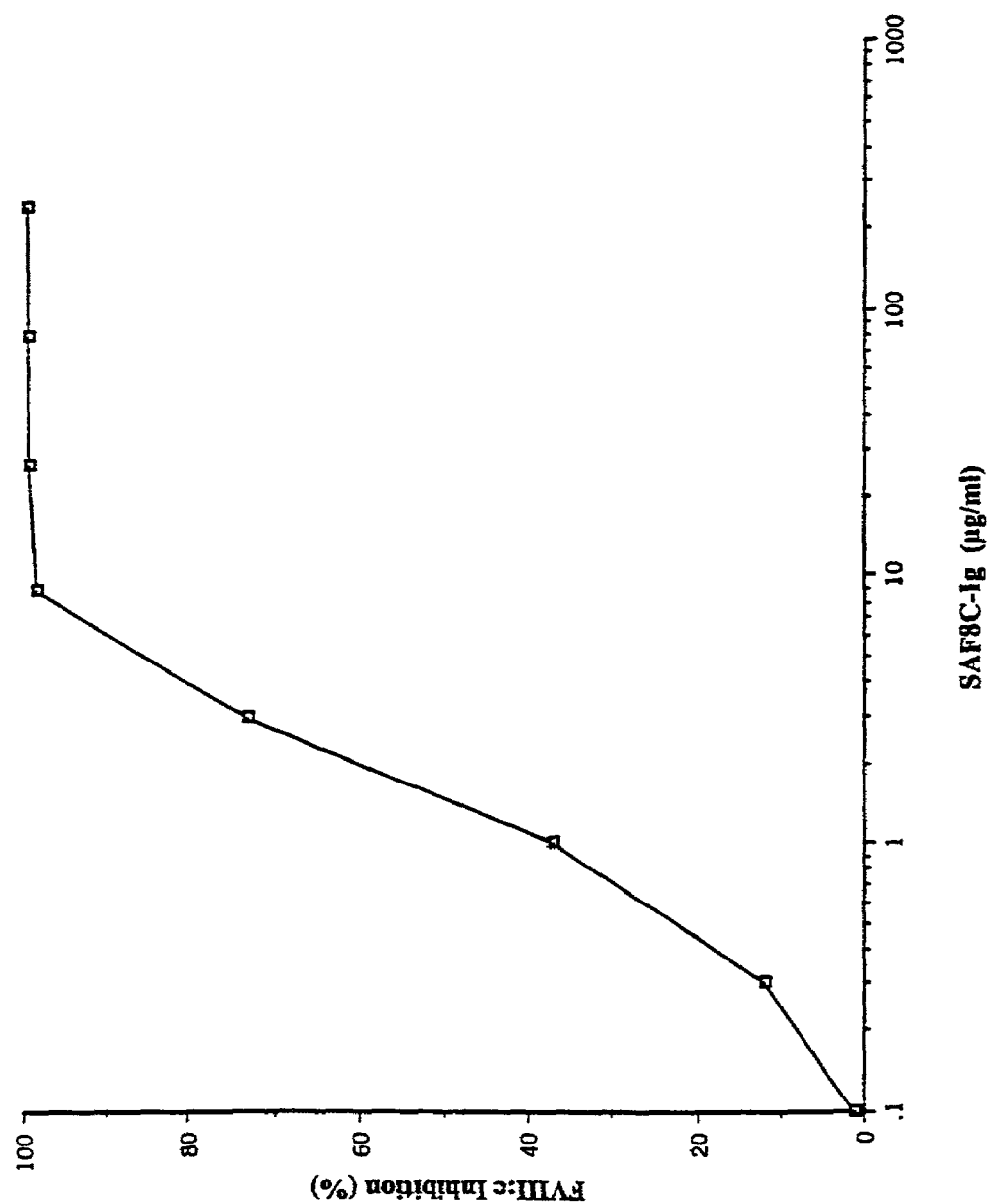
FIG. 10 provides a graph showing inhibition of factor VIII activity by the antibody SAF8C-Ig mentioned in WO97/26010

Levels of factor VIII are measured in a functional assay following an incubation period of two hours at 37° C. with various concentrations of the antibody SAF8C-Ig, using the chromogenic assay described in example 1. As shown in FIG. 10, the residual factor VIII activity is reduced in a dose dependent manner. Already at 100 microgr/ml of SAF8C-Ig, residual factor VIII activity is less than 1% of the normal activity. Such low factor VIII levels expose the patient to a high risk of spontaneous bleedings, as is well known for instance from Levine, *Ann. NY Acad. Sci.* (1975) 240:201 and Gilbert, *Mount Sinai J. Med.* (1977) 44: 339.

EXAMPLE 7

Inhibition of Venous Thrombosis in Hamsters by KRIX 1.

Figure 11:
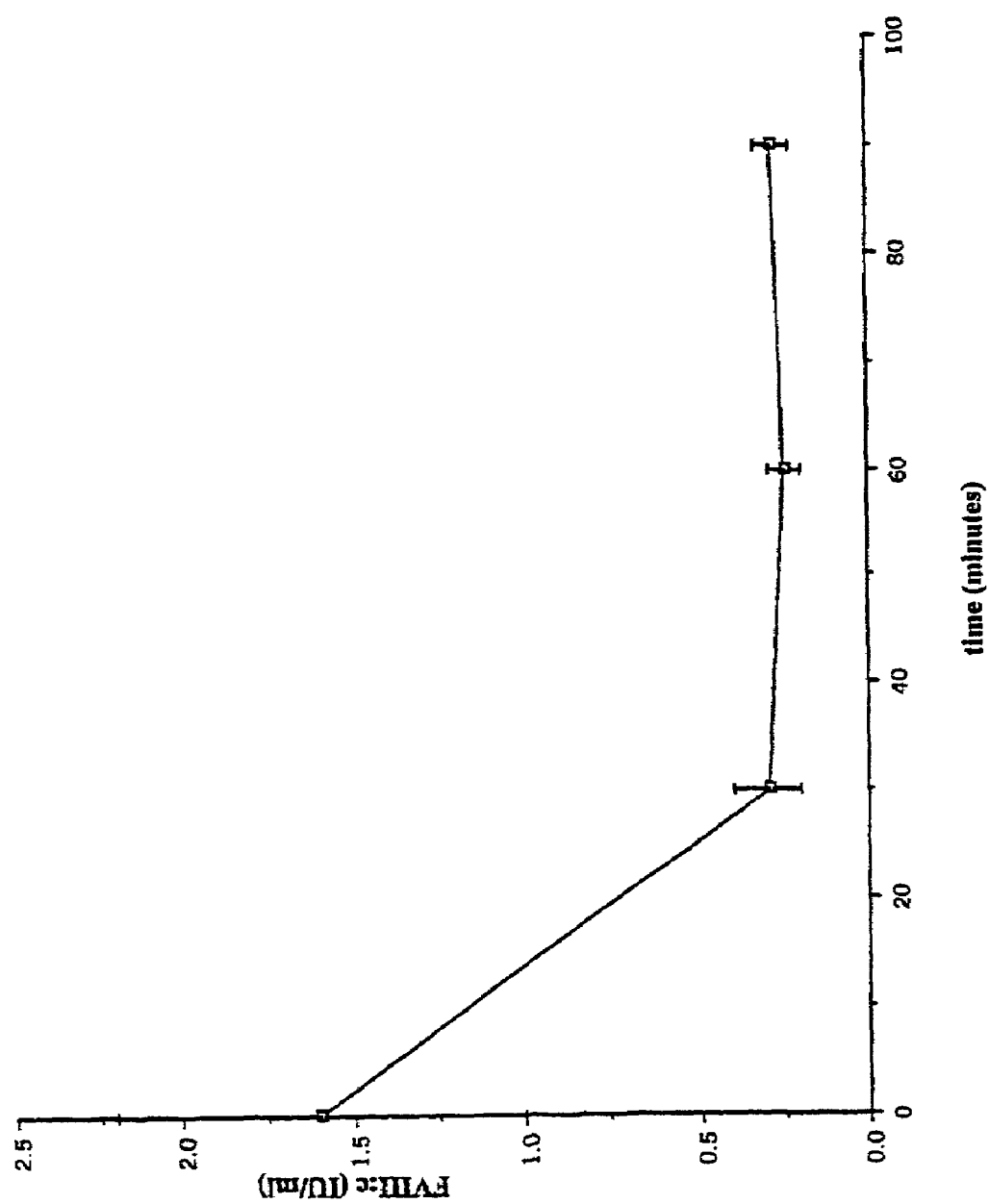
FIG. 11 illustrates the kinetics of factor VIII inhibition by KRIX-1.

Thrombosis was experimentally induced in the femoral vein of anesthetized hamsters, by injecting the dye rose-bengal in the jugular vein and by exposure of the femoral vein to the green light of a Xenon lamp for 4 minutes (Kawazaki et al. *Thromb Haemost* (1999) 81: 306–11). As a consequence of illumination of the vessel, the dye decomposes and generates radicals injuring the vessel endothelial cells. Thus, subendothelial structures are exposed to the blood circulation and thrombus formation is initiated. The amount of thrombus formed is measured via transillumination of the injured vessel (Kawazaki et al. *Thromb Haemost* (1999) 81: 306–11) and is quantified via the amount of white light being transillumnated through the vessel. As represented in FIG. 11, when this experiment is performed in control animals, the average thrombus size measured in 13 hamsters is 220,000±32,575 (mean±SEM) Arbitrary light Units (A.U.), whereas treatment of a group of 12 hamsters with KRIX-1 (400–800 microgr/kg, given as a bolus immediately prior to induction of thrombosis) reduced the mean thrombus size to 122,000±27,100 A. U. (p=0.0188, Mann-Whitney test).

Figure 12:
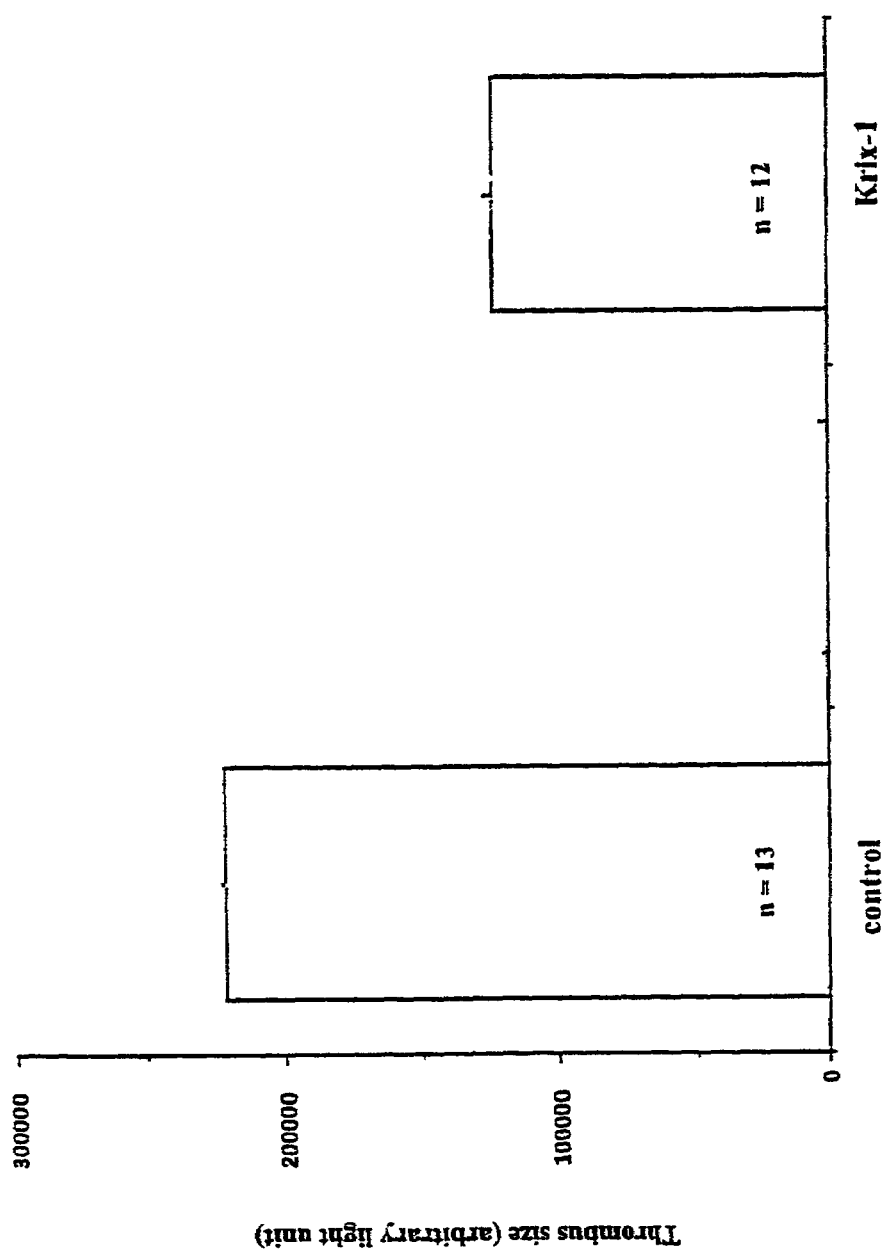
FIG. 12 illustrates the inhibition of venous thrombosis in a hamsters model by KRIX-1.

Additionally, the kinetics of factor VIII inhibition by KRIX-1 was analyzed ex-vivo as follows: hamsters were injected intravenously with KRIX-1(1600 microgr/kg). Levels of factor VIII:c were measured in a chromogenic assay (*Coatest Factor VIII$^R$* (Chromogenix AB, Mölndal, Sweden), and *Factor VIII Chromogenic Assay* (Dade, Düdingen, Switzerland)) using plasma collected before and at different periods of time after injection. FIG. 12 shows that in these hamsters, factor VIII activity is reduced from 1.6 IU/ml to 0.3 IU/ml already 30 minutes after antibody injection, thus confirming that KRIX-1 only partially inhibits factor VIII.

---

What is claimed is:

1. A purified monoclonal antibody produced by the cell line named KRIX 1 deposited with the Belgian Coordinated Collections of Micro-organisms, under accession number LMBP 5089CB.

2. An antigen-binding fragment Fab, Fab', F(ab')$_2$ or scFV, of a monoclonal antibody according to claim 1, said fragment binding the C1 domain of fVIII and having the capacity to partially inhibit fVIII activity.

3. A cell line named KRIX 1 deposited with the Belgian Coordinated Collections of Micro-organisms, under accession number LMBP 5089CB.

SEQUENCE LISTING

<160> NUMBER OF SEQ ID NOS: 8

<210> SEQ ID NO 1
<211> LENGTH: 143
<212> TYPE: PRT
<213> ORGANISM: Homo sapiens

<400> SEQUENCE: 1

```
Met Glu Thr Pro Ala Gln Leu Leu Phe Leu Leu Leu Trp Leu Pro
1               5                   10                  15

Asp Thr Thr Gly Glu Ile Val Leu Thr Gln Phe Pro Gly Thr Leu Ser
                20                  25                  30

Leu Ser Pro Gly Glu Arg Ala Thr Leu Ser Cys Arg Ala Ser Gln Ser
                35                  40                  45

Val Ala Ser Ala Tyr Leu Ala Trp Tyr Gln Gln Lys Pro Gly Gln Ala
    50                  55                  60

Pro Arg Leu Leu Ile Tyr Gly Ala Ser Ser Arg Ala Thr Asp Ile Pro
65                  70                  75                  80

His Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
                100                 105                 110

Gly Thr Ser Ala Leu Leu Thr Phe Gly Gly Gly Thr Lys Val Glu Ile
            115                 120                 125

Lys Arg Thr Val Ala Ala Pro Ser Val Phe Ile Phe Pro Pro Ser
    130                 135                 140
```

<210> SEQ ID NO 2
<211> LENGTH: 150
<212> TYPE: PRT
<213> ORGANISM: Homo sapiens

<400> SEQUENCE: 2

```
Met Asp Trp Thr Trp Arg Ile Leu Phe Leu Val Ala Ala Thr Gly
1               5                   10                  15

Thr His Ala Gln Val Gln Leu Val Gln Ser Gly Ala Glu Val Lys Lys
                20                  25                  30

Pro Gly Ala Ser Val Lys Val Ser Cys Lys Val Ser Gly Tyr Thr Leu
```

-continued

```
                35                  40                  45
Thr Glu Leu Pro Val His Trp Val Gly Gln Ala Pro Gly Lys Gly Leu
     50                  55                  60

Glu Trp Val Gly Ser Phe Asp Pro Glu Ser Gly Glu Ser Ile Tyr Ala
65                  70                  75                  80

Arg Glu Phe Gln Gly Ser Val Thr Met Thr Ala Asp Thr Ser Thr Asp
                85                  90                  95

Ile Ala Tyr Met Glu Leu Ser Ser Leu Arg Ser Asp Asp Thr Ala Val
            100                 105                 110

Tyr Tyr Cys Ala Val Pro Asp Pro Asp Ala Phe Asp Ile Trp Gly Gln
        115                 120                 125

Gly Thr Met Val Thr Val Ser Ser Ala Ser Thr Lys Gly Pro Ser Val
    130                 135                 140

Phe Pro Leu Gly Ser Arg
145                 150
```

<210> SEQ ID NO 3
<211> LENGTH: 142
<212> TYPE: PRT
<213> ORGANISM: Homo sapiens

<400> SEQUENCE: 3

```
Met Glu Thr Pro Ala Gln Leu Leu Phe Leu Leu Leu Leu Trp Leu Pro
1               5                   10                  15

Asp Thr Thr Gly Glu Ile Ala Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Phe Ser Ser Ser Tyr Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Lys Tyr
            100                 105                 110

Gly Thr Ser Ala Ile Thr Phe Gly Gln Gly Thr Arg Leu Glu Ile Lys
        115                 120                 125

Gly Thr Val Ala Ala Pro Ser Val Phe Ile Phe Pro Pro Ser
    130                 135                 140
```

<210> SEQ ID NO 4
<211> LENGTH: 429
<212> TYPE: DNA
<213> ORGANISM: Homo sapiens
<220> FEATURE:
<221> NAME/KEY: V_region
<222> LOCATION: (1)..(429)
<223> OTHER INFORMATION:
<221> NAME/KEY: misc_feature
<222> LOCATION: (127)..(162)
<223> OTHER INFORMATION: complementary determining region number one
<221> NAME/KEY: misc_feature
<222> LOCATION: (205)..(225)
<223> OTHER INFORMATION: complementary determining region number two
<221> NAME/KEY: misc_feature
<222> LOCATION: (325)..(354)
<223> OTHER INFORMATION: complementary determining region number three

<400> SEQUENCE: 4

-continued

```
atggaaaccc cagctcagct tctcttcctc ctgctactct ggctcccaga taccaccgga    60
gaaattgtgt tgacgcagtt cccaggcacc ctgtctttgt ctccagggga aagagccacc   120
ctctcctgca gggccagtca gagtgttgcc agcgcctact tagcctggta ccagcaaaaa   180
cctggccagg ctcccaggct cctcatctat ggtgcatcca gtagggccac cgacatccca   240
cacaggttca gtggcagtgg gtctgggaca gacttcactc tcaccatcag cagactggag   300
cctgaagatt ttgcagtgta ctactgtcag caatatggta cctcagcctt actcactttc   360
ggcggaggga ccaaggtgga gatcaaacga actgtggctg caccatctgt cttcatcttc   420
ccgccatct                                                          429
```

<210> SEQ ID NO 5
<211> LENGTH: 450
<212> TYPE: DNA
<213> ORGANISM: Homo sapiens
<220> FEATURE:
<221> NAME/KEY: V_region
<222> LOCATION: (1)..(450)
<223> OTHER INFORMATION:
<221> NAME/KEY: misc_feature
<222> LOCATION: (130)..(159)
<223> OTHER INFORMATION: complementary determining region number one
<221> NAME/KEY: misc_feature
<222> LOCATION: (202)..(258)
<223> OTHER INFORMATION: complementary determining region number two
<221> NAME/KEY: misc_feature
<222> LOCATION: (343)..(375)
<223> OTHER INFORMATION: complementary determining region number three

<400> SEQUENCE: 5

```
atggactgga cctggaggat cctcttcttg gtggcagcag ctacaggcac ccacgcccag    60
gtccaactgg tacagtctgg ggctgaggtg aagaagcctg ggcctcagt gaaggtctcc    120 tgcaaggttt ccggatacac cctcactgaa ttacccgtgc actgggtcgg acaggctcct   180
ggaaaagggc ttgagtgggt gggaagtttt gatcctgaaa gtgagaatc aatctacgca   240 cgggagttcc agggcagcgt caccatgacc gcggacacat ctacagacat agcctacatg   300
gagctgagca gcctgagatc tgacgacacg gccgtgtatt actgtgcagt ccctgaccct   360
gatgcttttg atatctgggg ccaagggaca atggtcaccg tctcttcagc ctccaccaag   420
ggcccatcgg tcttccccct gggatcccgt                                    450
```

<210> SEQ ID NO 6
<211> LENGTH: 426
<212> TYPE: DNA
<213> ORGANISM: Homo sapiens
<220> FEATURE:
<221> NAME/KEY: V_region
<222> LOCATION: (1)..(426)
<223> OTHER INFORMATION:
<221> NAME/KEY: misc_feature
<222> LOCATION: (7)..(162)
<223> OTHER INFORMATION: complementary determining region number one
<221> NAME/KEY: misc_feature
<222> LOCATION: (205)..(225)
<223> OTHER INFORMATION: complementary determining region number two
<221> NAME/KEY: misc_feature
<222> LOCATION: (325)..(351)
<223> OTHER INFORMATION: complementary determining region number three

<400> SEQUENCE: 6

```
atggaaaccc cagctcagct tctcttcctc ctgctactct ggctcccaga taccaccgga    60
gaaattgcgt tgacgcagtc tccaggcacc ctgtctttgt ctccagggga aagagccacc   120
ctctcctgca gggccagtca gagttttagc agcagctact tagcctggta tcagcagaaa   180
```

```
cctggccagg ctcccaggct cctcatctat ggtgcatcca ccagggccac tggcatccca    240
gacaggttca gtggcagtgg gtctgggaca gacttcactc tcaccatcag cagactggag    300
cctgaagatt ttgcagtgta ttactgtcag aagtatggta cgtcagcgat caccttcggg    360
caagggacac gactggagat taaggaact gtggctgcac catctgtctt catcttcccg    420
ccatct                                                               426
```

```
<210> SEQ ID NO 7
<211> LENGTH: 468
<212> TYPE: DNA
<213> ORGANISM: Homo sapiens
<220> FEATURE:
<221> NAME/KEY: V_region
<222> LOCATION: (1)..(468)
<223> OTHER INFORMATION:
<221> NAME/KEY: misc_feature
<222> LOCATION: (124)..(192)
<223> OTHER INFORMATION: complementary determining region number one
<221> NAME/KEY: misc_feature
<222> LOCATION: (232)..(285)
<223> OTHER INFORMATION: complementary determining region number two
<221> NAME/KEY: misc_feature
<222> LOCATION: (282)..(435)
<223> OTHER INFORMATION: complementary determining region number three

<400> SEQUENCE: 7
```

```
atggactgga cctggaggat cctcttcttg gtggcagcag ccacaggagc ccactcccag     60
gtgcaactgg tgcaatctgg ggctgaggtg aagaagcctg gggcctcagt gaaggtctcc    120
tgcaagacct ctggatacaa cttcaccggc tactctgctt ctggacatat cttcaccgcc    180
tactctgtgc actgggtgcg acaggcccct ggacaagggc ttgagtggat gggaaggatc    240
aaccctaaca gtggtgccac agactatgca cataaatttc agggcagggt caccatgtcc    300
agggacacgt ccatcagcac agcctacatg gaactgagca ggctgacatc tgacgacacg    360
gccatgtatt actgtgcgag agccgacaac tatttcgata ttgtgactgg ctatacttct    420
cattactttg actactgggg ccggggaacc ctggtcaccg tctcctca                 468
```

```
<210> SEQ ID NO 8
<211> LENGTH: 156
<212> TYPE: PRT
<213> ORGANISM: Homo sapiens

<400> SEQUENCE: 8

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Thr Ser Gly Tyr Asn Phe
        35                  40                  45

Thr Gly Tyr Ser Ala Ser Gly His Ile Phe Thr Ala Tyr Ser Val His
    50                  55                  60

Trp Val Arg Gln Ala Pro Gly Gln Gly Leu Glu Trp Met Gly Arg Ile
65                  70                  75                  80

Asn Pro Asn Ser Gly Ala Thr Asp Tyr Ala His Lys Phe Gln Gly Arg
                85                  90                  95

Val Thr Met Ser Arg Asp Thr Ser Ile Ser Thr Ala Tyr Met Glu Leu
            100                 105                 110

Ser Arg Leu Thr Ser Asp Asp Thr Ala Met Tyr Tyr Cys Ala Arg Ala
        115                 120                 125
```

```
Asp Asn Tyr Phe Asp Ile Val Thr Gly Tyr Thr Ser His Tyr Phe Asp
    130                 135                 140

Tyr Trp Gly Arg Gly Thr Leu Val Thr Val Ser Ser
145             150                 155
```